(12) United States Patent
Wan et al.

(10) Patent No.: US 9,073,952 B1
(45) Date of Patent: Jul. 7, 2015

(54) SYNTHESIS METHOD FOR CARBOSILANES

(75) Inventors: Zhiwen Wan, Plano, TX (US); Ziyun Wang, Allen, TX (US); Ashutosh Misra, Plano, TX (US); Jean-Marc Girard, Tokyo (JP); Andrey V. Korolev, Newark, DE (US)

(73) Assignees: L'Air Liquide, Société Anonyme pour l'Etude et l'Exploitation des Procédés Georges Claude, Paris (FR); American Air Liquide, Inc., Fremont, CA (US); Air Liquide Electronics U.S. LP, Dallas, TX (US)

( * ) Notice: Subject to any disclaimer, the term of this patent is extended or adjusted under 35 U.S.C. 154(b) by 217 days.

(21) Appl. No.: 13/458,579

(22) Filed: Apr. 27, 2012

(51) Int. Cl.
C07F 7/18 (2006.01)
C07F 7/08 (2006.01)
C07F 7/12 (2006.01)

(52) U.S. Cl.
CPC ............. C07F 7/1868 (2013.01); C07F 7/0827 (2013.01); C07F 7/125 (2013.01)

(58) Field of Classification Search
CPC ..... C08F 4/6578; C08F 4/6355; C07F 7/1868
USPC .................................. 556/431, 465, 478, 480
See application file for complete search history.

(56) References Cited

U.S. PATENT DOCUMENTS

| | | | | |
|---|---|---|---|---|
| 5,153,295 | A * | 10/1992 | Whitmarsh et al. | 528/31 |
| 6,521,774 | B2 * | 2/2003 | Koike et al. | 556/435 |
| 6,730,802 | B2 * | 5/2004 | Shen et al. | 556/12 |
| 6,800,133 | B1 | 10/2004 | Kim et al. | |
| 2002/0002299 | A1 * | 1/2002 | Arkles et al. | 556/478 |
| 2013/0274497 | A1 | 10/2013 | Larson et al. | |

FOREIGN PATENT DOCUMENTS

WO   WO 95 10638   4/1995

OTHER PUBLICATIONS

Bazant et al; Collection czechoslov. Chemical Communication, 1974, vol. 39, 1735-1739.*
Birot, M. et al., "Comprehensive chemistry of polycarbosilanes, polysilazanes, and polycarbosilazanes as precursors of ceramics," Chem. Rev. 1995, 95, pp. 1443-1477.
Bobrovsky, A.Y. et al., "Photochemical and photoorientational behavior of liquid crystaliine carbosilane dendrimer with azobenzene terminal groups," J. Phys. Chem. B 2002, 106, pp. 540-546.
Boo, J.-H. et al., "Epitaxial growth of cubic SiC thin films on silicon using single molecular precursors by metalorganic chemical vapor deposition," J. Vac. Sci. Technol. A 19(4), Jul./Aug. 2001, pp. 1887-1893.
Brefort, J.L. et al., "New poly[(silylene)diacetylenes] and poly[(germylene) diacetylenes]: Synthesis and conductive properties," Organometallics 1992, 11, pp. 2500-2506.
Brondani, D.J. et al., "A new trialkoxysilylation reaction, the cross-coupling of (tri-isopropyloxysilyl)methyl grignard reagent with organic halides," J. Org. Chem., 1993, vol. 451, pp. C1-C3.
Brondani, D.J. et al., "Polyfunctional carbosilanes and organosilicon compounds, syntheses via Grignard reactions," Tetrahedron Letters, 34, 13, 1993, pp. 2111-2114.
Corriu, R.J.P. et al., "One-step route to silicon carbide precursors by a tunable catalytic polycondensation," Chem. Mater. 1994, 6, pp. 15-17.
Daiss, J.O. et al., "Synthesis of the multifunctional (chloromethyl)silanes $Cl_2Si(CH_2Cl)_2$, $(MeO)_2Si(CH_2Cl)_2$, $RSi(SCH_2Cl)_3$ (R=2,4,6-trimethoxyphenyl), $ClSi(CH_2Cl)_3$, $MeOSi(CH_2Cl)_3$, $Si(CH_2Cl)_4$, and $ClCH_2CH_2Si(CH_2Cl)_3$§" Organometallics 2004, 23, p. 5193-5197.
Dannels, B.F. et al., "Studies in organosilicon chemistry. XXXIV. The reaction of trimethylsilylmethyl metallic compounds with trichlorosilane," vol. 22, 1956, pp. 748-750.
Gevorgyan, V. et al., "Silatranes from reactions of chloromethylsilatrane with chlorosilanes and magnesium in tetrahydrofuran," J. Org. Chem., 1991, vol. 418, pp. C21-C23.
Han, W.-S. et at., "Silane-based hydrogen storage materials for fuel cell application: Hydrogen release via methanolysis and regeneration by hydride reduction from organosilanes," Int'l Journal of Hydrogen Energy 36, 2001, pp. 12305-12312.
Handmank, V.I. et al., "New bicyclic sila-heterocycles: Syntheses and crystal structure analyses of rac-7-ethoxy-2,2-diorganyl-2,3,4,5a-tetrahydro-1H-3a,6-diaza-2-sila-inden-4-ones," Journal of Organometallic Chemistry 613, 2000, pp. 19-25.
Hong, S.H. et al., "Phosohine-catalyzed Si—C coupling of bis-silylmethanes: Preparation of cyclic $(Cl_2SiCH_2)_2$ and linear $Cl_2Si(CH_2SiC1_3)_2$ via silylene and silene intermediates," Organometallics 2010, 29, pp. 687-691.
Jung, I.N. et al., "Direct synthesis of trisilaalkanes," Bull. Korean Chem. Soc., 12, 4, 1961, pp. 445-449.
Kang, S.-H. et al., "Phosphonium chloride-catalyzed dehydrochiorinative coupling reactions of alkyl halides with hydridochlorosilanes," Organometallics 2003, 22, pp. 529-534.
Laine, R.M., "Preceramic polymer routes to silicon carbide," Chem. Mater. 1993, 5, pp. 260-279.
Lee, T. et al., "Highly efficient hydrosilylation of diyne and triyne π-electron bridges: Its application to fluorescent dyes and silylene-spaced vinylarene compounds," Organometallics 2004, 23, pp. 4184-4191.
Li, C.-F. et al., "Photoluminescense of PMMA doped with fluorescein and carbosilane dendrimer and lasiing PBG resonance cavity," Journal of Luminescense 127, 2007, pp. 321-326.
Mirskov, R.G. et al., "High-purity alkoxychlorosilanes as precursors for precipitation of silica," Doklady Chemistry, 2008, vol. 421, Part 2, pp. 194-196.
Ohshita, J. et al., "Polymeric organosilicon systems. 11. Synthesis and some properties of poly(disilanylenebutenyne-1,4-diy1s) and poly[(methylphenylsilylen)butenyne-1,4-diy1]¹," Macromolecules 1992, 25, pp. 2134-2140.
Seyferth, D., "Polycarbosilanes: an overview," Inorganic and Organometallic Polymers, Chapter 3, ACS Symposium Series 360, ACS: Washington, DC, 1988, pp. 21-42.

(Continued)

*Primary Examiner* — Sudhakar Katakam
*Assistant Examiner* — Pancham Bakshi
(74) *Attorney, Agent, or Firm* — Patricia E. McQueeney

(57) ABSTRACT

$Si(OEt)_2[CH_2—Si(OEt)_3]_2$ compounds are synthesized by reacting a Grignard reagent having the formula $Si(OEt)_3(CH_2MgCl)$ with a quenching agent having the formula $Si(OEt)_2Cl_2$.

4 Claims, 2 Drawing Sheets

(56) References Cited

OTHER PUBLICATIONS

Son, H.-J. et al., "Electrochemical deposition of end-capped triarylamine and carbazole dendrimers: Alternate technique for the manufacture of multilayer films," Chem. Mater. 18, 25, Dec. 12, 2006, pp. 5811-5813.

Speier, J.L. et al., "Relative consecutive competitive rates of alkoxylation of chlorosilanes," Organometallics 1993, 12, pp. 1981-1982.

Whitmarsh, C.K. et al., "Synthesis and structure of a highly branched polycarbosilane derived from (chloromethyl)trichlorosilane," Organometallics 1991, 10, pp. 1336-1344.

Yoo, B.R. et al., "Synthesis of organosilicon compounds by new direct reactions," Advances in Organometallic Chemistry, 2005, vol. 50, pp. 145-177.

Hassler, K. et al., "The (chloromethyl)dihalosilanes $X_2HSiCH_2Cl$ (X=F, Cl, Br, I): synthesis, multinuclear NMR spectroscopy and rotational isomerism examined by Raman spectroscopy," Eur. J. lnorg. Chem. 2004, pp. 4259-4265.

Jung et al., "Si-C coupling reaction of polychloromethanes with $HSiCl_3$ in the presence of $Bu_4PCl$: Convenient synthetic method for bis(chlorosilyl)methanes," Journal of Organometallic Chemistry (2007) 692(18) 3901-3906.

Seyferth, D. et al., "The preparation of chloromethyl derivatives of germanium and silicon by the diazomethane method," Journal of American Chemical Society, 1955, 77(4), pp. 907-908.

Shimizu et al., "1,1,3,3-tetrakis(alkylthio)-1,3-dilithio-2-silapropanes: useful reagents for the synthesis of polysilacycloalkanes via dianionic ring formation," Arkivoc (2007) 29-48.

\* cited by examiner

SYNTHESIS METHOD FOR CARBOSILANES

TECHNICAL FIELD

Disclosed are synthesis methods to produce carbosilanes.

BACKGROUND

Carbosilanes, i.e. linear or branched molecules with a backbone having alternate Si and C atoms and at least one Si—C—Si unit, are attracting attention owing to their chemical properties and potential usage in various fields such as ceramics, optical coatings, electronics, semiconductors, and hydrogen storage.

However, the synthesis of such compounds has proven to be relatively difficult, partially due to the fact that a mixture of compounds may be produced. In addition the low yield of such methods increases the cost of making the targeted compound.

Controlled Si—C—Si unit synthesis has been achieved using a Grignard method. Gevorgyan et al. (J. Org. Chem. 418, 1991 C21-C23) disclose the formation of $R_3Si$—$CH_2$—$Si(OCH2CH2)_3N$ from $ClCH_2$—$Si(OCH_2CH_2)_3N$ and $R_3Si$—Cl in the presence of magnesium in THF, with $R_3$ being $Me_3$, $Me_2Ph$, $MePh_2$, $HMe_2$, or $HMePh$. Brondani et al. (J. Org. Chem. 451, 1993 C1-C3) disclose cross-coupling of (tri-isopropyloxysilyl)methyl Grignard reagents with organic halides to form trialkoxysilylated organic compounds. U.S. Pat. No. 5,153,295 to Whitmarsh et al. discloses that the diethylamino group of a $ClSi(NEt_2)_2CH_2Cl$ Grignard reagent blocks two chlorine sites preventing branching of the carbosilane polymer. U.S. Pat. No. 6,730,802 to Shen et al. discloses synthesis of 2,4,6-trimethyl-2,4,6-trisilaheptane by reducing chloromethyl-dimethylchlorosilane with lithium aluminum hydride, reacting the resulting chloromethyldimethylsilane with magnesium to form the corresponding Grignard reagent, and coupling the Grignard reagent with methyldichlorosilane.

For some specific applications, obtaining a pure product is critical for the stability of the process that uses the product, and such non-discriminating synthesis methods are costly since they involve expensive separation processes to obtain the target compound. A need remains for a cost effective synthesis method of linear or branched carbosilanes.

NOTATION AND NOMENCLATURE

Certain abbreviations, symbols, and terms are used throughout the following description and claims, and include:

As used herein, the term "carbosilane" refers to a linear or branched molecule with a backbone having alternate Si and C atoms and at least one Si—C—Si unit; the term "Grignard reagent" refers to organomagnesium halides having the formula $Si(OR')_xH_yR_z(CH_2MgX)$, wherein $x=0$ to 3; $y=0$ to 1; $z=0$ to 3; $x+y+z=3$; $X$=Cl, Br, or I; each R is independently a C1 to C5 linear or branched alkyl group or a trimethylsilyl group; and each R' is independently a C1 to C5 linear or branched alkyl group, even though the claimed Grignard reagents are not used in a Grignard reaction; the term "quenching" refers to the reaction of the Grignard reagent with the quenching agent; the term "quenching agent" refers to the compound that "deactivates" the Grignard reagent by reacting with the Grignard reagent to produce a Mg salt compound.

As used herein, the term "alkyl group" refers to saturated functional groups containing exclusively carbon and hydrogen atoms. Further, the term "alkyl group" refers to linear, branched, or cyclic alkyl groups. Examples of linear alkyl groups include without limitation, methyl groups, ethyl groups, propyl groups, butyl groups, pentyl groups, etc. Examples of branched alkyls groups include without limitation t-butyl. Examples of cyclic alkyl groups include without limitation, cyclopropyl groups, cyclopentyl groups, cyclohexyl groups, etc.

As used herein, the abbreviation "Me" refers to a methyl group; the abbreviation "Et" refers to an ethyl group; the abbreviation "Pr" refers to a n-propyl group; the abbreviation "Pr" refers to an isopropyl group; the abbreviation "nBu" refers to n-butyl, the abbreviation "tBu" refers to a tert-butyl; and the abbreviation "sBu" refers to a sec-butyl.

The standard abbreviations of the elements from the periodic table of elements are used herein. It should be understood that elements may be referred to by these abbreviations (e.g., Ni refers to nickel, Si refers to silicon, C refers to carbon, etc.).

SUMMARY

Disclosed are methods of synthesizing a carbosilane compound by reacting a Grignard reagent having the formula $Si(OR')_xH_yR_z(CH_2MgX)$ with a quenching agent having the formula $SiCl_a(OR)_b(H)_c$ to produce $Si(OR)_b(H)_c[CH_2$—$Si(OR')_xH_yR_z]_a$, wherein $a=1$ to 3; $b=0$ to 3; $c=0$ to 2; $a+b+c=4$; $x=0$ to 3; $y=0$ to 1; $z=0$ to 3; $x+y+z=3$; $X$=Cl, Br, or I; each R is independently a C1 to C5 linear or branched alkyl group or a trimethylsilyl group; and each R' is independently a C1 to C5 linear or branched alkyl group. The disclosed methods may further include one or more of the following aspects:

- a molar ratio of the Grignard reagent $Si(OR')_xH_yR_z(CH_2MgX)$ to the quenching agent $SiCl_a(OR)_b(H)_c$ is between approximately 0.8 and approximately 4.5;
- forming the Grignard reagent $Si(OR')_xH_yR_z(CH_2MgX)$ in-situ by reacting $Si(OR')_xH_yR_z(CH_2X)$ over magnesium;
- the step of forming the Grignard reagent $Si(OR')_xH_yR_z(CH_2MgX)$ occurring in a same vessel as the step of reacting the Grignard reagent and the quenching agent;
- reducing $Si(OR)_b(H)_c[CH_2$—$Si(OR')_xH_yR_z]_a$ by $AlLiH_4$ in ether to form a compound having a formula $SiH_{b+c}[CH_2$—$SiH_{x+y}R_z]_{4-b-c}$, wherein $b=0$ to 3; $c=0$ to 2; $b+c=1$ to 3; $x=0$ to 3; $y=0$ to 1; $z=0$ to 3; $x+y+z=3$; and each R is independently a C1 to C5 linear or branched alkyl group or a trimethylsilyl group;
- a molar ratio of $AlLiH_4$ to $Si(OR)_b(H)_c[CH_2$—$Si(OR')_xH_yR_z]_a$ being between approximately $(b+ax)/4$ and approximately $(b+ax)/2$, wherein $b=0$ to 3, $a=1$ to 3, and $x=0$ to 3;
- reducing $Si(OR)_b(H)_c[CH_2$—$Si(OR')_xH_yR_z]_a$ by $NaBH_4$ in ether to form $SiH_{b+c}[CH_2$—$SiH_{x+y}R_z]_{4-b-c}$, wherein $b=0$ to 3; $c=0$ to 2; $b+c=1$ to 3; $x=0$ to 3; $y=0$ to 1; $z=0$ to 3; $x+y+z=3$; and each R is independently a C1 to C5 linear or branched alkyl group or a trimethylsilyl group;
- a molar ratio of $NaBH_4$ to $Si(OR)_b(H)_c[CH_2$—$Si(OR')_xH_yR_z]_a$ being between approximately $(b+ax)/4$ and approximately $(b+ax)/2$, wherein $b=0$ to 3, $a=1$ to 3, and $x=0$ to 3;
- $x=3$, $y=0$, $z=0$, and R'=Me or Et;
- the Grignard reagent being $Si(OR')_3(CH_2MgCl)$;
- $a=2$, $b=2$, and $c=0$;
- the quenching agent being $Si(OEt)_2Cl_2$;
- $y=1$ and $b=0$;
- $z=0$ and $c=2$;
- the quenching agent being $SiH_2Cl_2$; and
- $b=0$ and $c=2$.

Also disclosed are methods of synthesizing a carbosilane compound by in situ quenching of a Grignard reagent having the formula $Si(OR')_xH_yR_z(CH_2MgX)$ with a quenching agent having the formula $SiCl_a(OR)_b(H)_c$ to produce $Si(OR)_b(H)_c[CH_2-Si(OR')_xH_yR_z]_a$, wherein a=1 to 3; b=0 to 3; c=0 to 2; a+b+c=4; x=0 to 3; y=0 to 1; z=0 to 3; x+y+z=3; X=Cl, Br, or I; each R is independently a C1 to C5 linear or branched alkyl group or a trimethylsilyl group; and each R' is independently a C1 to C5 linear or branched alkyl group.

Also disclosed are methods of synthesizing a carbolsilane compound by reacting a Grignard reagent having the formula $Si(OEt)_3(CH_2MgCl)$ with a quenching agent having the formula $Si(OEt)_2Cl_2$ to produce $Si(OEt)_2[CH_2-Si(OEt)_3]_2$. The disclosed methods may further include one or more of the following aspects:

forming the Grignard reagent $Si(OEt)_3(CH_2MgCl)$ by reacting $Si(OEt)_3(CH_2X)$ over magnesium;

the step of forming the Grignard reagent $Si(OEt)_3(CH_2MgCl)$ occurring in a same vessel as the step of reacting the Grignard reagent and the quenching agent; and reducing $Si(OEt)_2[CH_2-Si(OEt)_3]_2$ to form a compound having a formula $SiH_2[CH_2-SiH_3]_2$.

BRIEF DESCRIPTION OF THE FIGURES

For a further understanding of the nature and objects of the present invention, reference should be made to the following detailed description, taken in conjunction with the accompanying figure wherein.

DETAILED DESCRIPTION OF PREFERRED EMBODIMENTS

Figure 1:
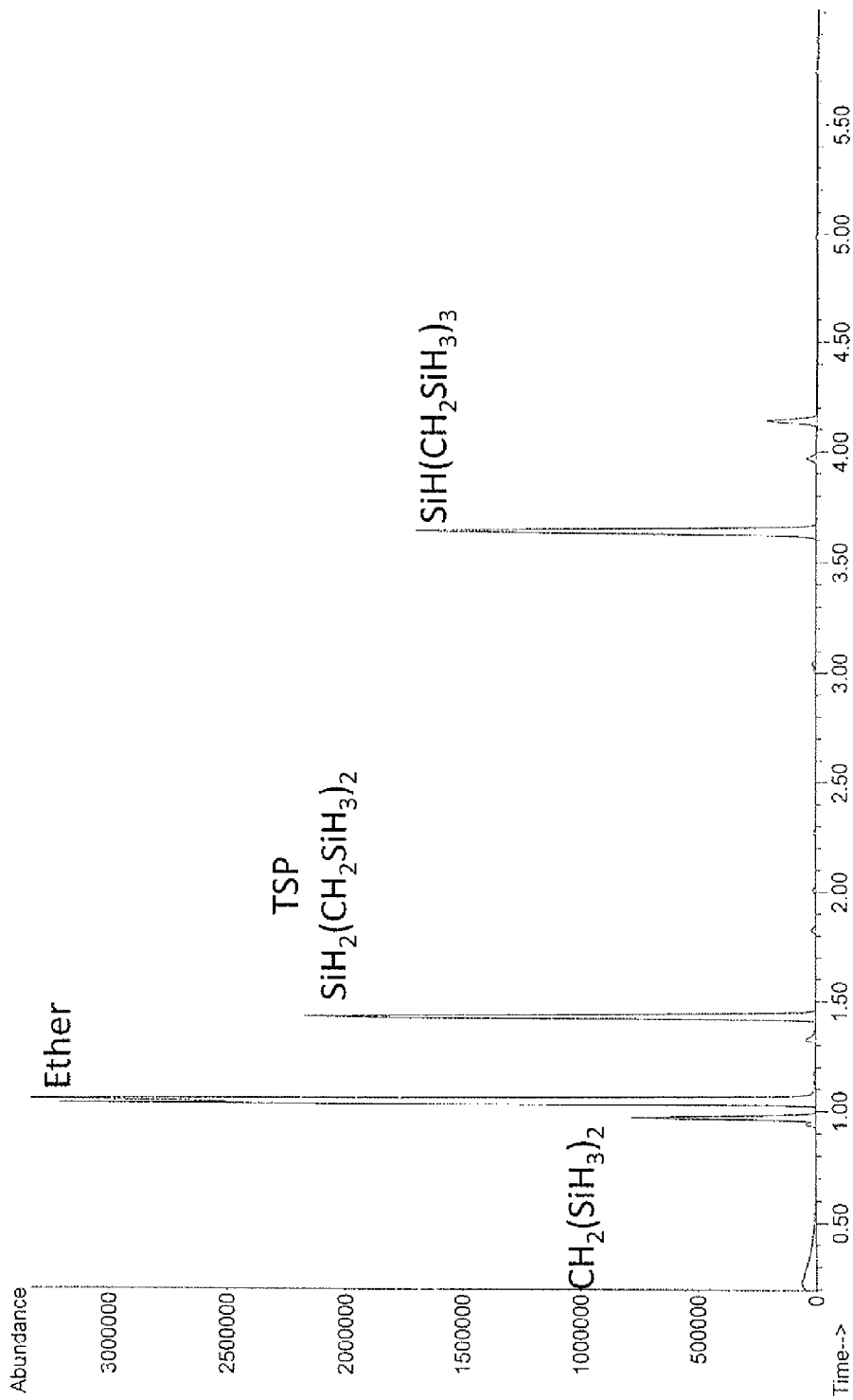
FIG. 1 is a gas chromatograph/mass spectrometer (GC/MS) graph of the product synthesized in the Comparative Example.

Disclosed are methods of synthesizing compounds having the formula $Si(OR)_b(H)_c[CH_2-Si(OR')_xH_yR_z]_a$, wherein a=1 to 3; b=0 to 3; c=0 to 2; a+b+c=4; x=0 to 3; y=0 to 1; z=0 to 3; x+y+z=3; each R is independently a C1 to C5 linear or branched alkyl group or a trimethylsilyl group; and each R' is independently a C1 to C5 linear or branched alkyl group. These compounds may be used in the field of ceramics, optical coatings, electronics (i.e., devices), semiconductors (i.e., components), hydrogen storage, and semiconductor components that may be used at least in electronic devices.

In some embodiments, x=3, y=0, z=0, and R'=Me or Et to produce $Si(OR)_b(H)_c[CH_2-Si(OMe)_3]_a$ and $Si(OR)_b(H)_c[CH_2-Si(OEt)_3]_a$, wherein a=1 to 3; b=0 to 3; c=0 to 2; a+b+c=4; and each R is independently a C1 to C5 linear or branched alkyl group or a trimethylsilyl ($SiMe_3$) group.

Exemplary compounds wherein x=3, y=0, z=0, R'=Me or Et, a=3, b=0, and c=1 include $SiH[CH_2-Si(OMe)_3]_3$ and $SiH[CH_2-Si(OEt)_3]_3$.

Exemplary compounds wherein x=3, y=0, z=0, R'=Me or Et, a=3, b=1, and c=0 include $Si(OMe)[CH_2-Si(OMe)_3]_3$, $Si(OMe)[CH_2-Si(OEt)_3]_3$, $Si(OEt)[CH_2-Si(OMe)_3]_3$, $Si(OEt)[CH_2-Si(OEt)_3]_3$, $Si(OiPr)[CH_2-Si(OMe)_3]_3$, $Si(OiPr)[CH_2-Si(OEt)_3]_3$, $Si(OnPr)[CH_2-Si(OMe)_3]_3$, $Si(OnPr)[CH_2-Si(OEt)_3]_3$, $Si(OnBu)[CH_2-Si(OMe)_3]_3$, $Si(OnBu)[CH_2-Si(OEt)_3]_3$, $Si(OtBu)[CH_2-Si(OMe)_3]_3$, $Si(OtBu)[CH_2-Si(OEt)_3]_3$, $Si(OiBu)[CH_2-Si(OMe)_3]_3$, $Si(OiBu)[CH_2-Si(OEt)_3]_3$, $Si(OSiMe_3)[CH_2-Si(OMe)_3]_3$, and $Si(OSiMe_3)[CH_2-Si(OEt)_3]_3$.

Exemplary compounds wherein x=3, y=0, z=0, R'=Me or Et, a=2, b=0, and c=2 include $SiH_2[CH_2-Si(OMe)_3]_2$ and $SiH_2[CH_2-Si(OEt)_3]_2$.

Exemplary compounds wherein x=3, y=0, z=0, R'=Me or Et, a=2, b=2, and c=0 include $Si(OMe)_2[CH_2-Si(OMe)_3]_2$, $Si(OMe)_2[CH_2-Si(OEt)_3]_2$, $Si(OEt)_2[CH_2-Si(OMe)_3]_2$, $Si(OEt)_2[CH_2-Si(OEt)_3]_2$, $Si(OiPr)_2[CH_2-Si(OMe)_3]_2$, $Si(OiPr)_2[CH_2-Si(OEt)_3]_2$, $Si(OnPr)_2[CH_2-Si(OMe)_3]_2$, $Si(OnPr)_2[CH_2-Si(OEt)_3]_2$, $Si(OnBu)_2[CH_2-Si(OMe)_3]_2$, $Si(OnBu)_2[CH_2-Si(OEt)_3]_2$, $Si(OtBu)_2[CH_2-Si(OMe)_3]_2$, $Si(OtBu)_2[CH_2-Si(OEt)_3]_2$, $Si(OiBu)_2[CH_2-Si(OMe)_3]_2$, $Si(OiBu)_2[CH_2-Si(OEt)_3]_2$, $Si(OSiMe_3)_2[CH_2-Si(OMe)_3]_2$ and $Si(OSiMe_3)_2[CH_2-Si(OEt)_3]_2$.

Exemplary compounds wherein x=3, y=0, z=0, R'=Me or Et, a=2, b=1, and c=1 include $SiH(OMe)[CH_2-Si(OMe)_3]_2$, $SiH(OMe)[CH_2-Si(OEt)_3]_2$, $SiH(OEt)[CH_2-Si(OMe)_3]_2$, $SiH(OEt)[CH_2-Si(OEt)_3]_2$, $SiH(OiPr)[CH_2-Si(OMe)_3]_2$, $SiH(OiPr)[CH_2-Si(OEt)_3]_2$, $SiH(OnPr)[CH_2-Si(OMe)_3]_2$, $SiH(OnPr)[CH_2-Si(OEt)_3]_2$, $SiH(OnBu)[CH_2-Si(OMe)_3]_2$, $SiH(OnBu)[CH_2-Si(OEt)_3]_2$, $SiH(OtBu)[CH_2-Si(OMe)_3]_2$, $SiH(OtBu)[CH_2-Si(OEt)_3]_2$, $SiH(OiBu)[CH_2-Si(OMe)_3]_2$, $SiH(OiBu)[CH_2-Si(OEt)_3]_2$, $SiH_2(OSiMe_3)[CH_2-Si(OMe)_3]_2$, and $SiH(OSiMe_3)[CH_2-Si(OEt)_3]_2$.

Exemplary compounds wherein x=3, y=0, z=0, R'=Me or Et, a=1, b=1, and c=2 include $SiH_2(OMe)[CH_2-Si(OMe)_3]$, $SiH_2(OMe)[CH_2-Si(OEt)_3]$, $SiH_2(OEt)[CH_2-Si(OMe)_3]$, $SiH_2(OEt)[CH_2-Si(OEt)_3]$, $SiH_2(OiPr)[CH_2-Si(OMe)_3]$, $SiH_2(OiPr)[CH_2-Si(OEt)_3]$, $SiH_2(OnPr)[CH_2-Si(OMe)_3]$, $SiH_2(OnPr)[CH_2-Si(OEt)_3]$, $SiH_2(OnBu)[CH_2-Si(OMe)_3]$, $SiH_2(OnBu)[CH_2-Si(OEt)_3]$, $SiH_2(OtBu)[CH_2-Si(OMe)_3]$, $SiH_2(OtBu)[CH_2-Si(OEt)_3]$, $SiH_2(OiBu)[CH_2-Si(OMe)_3]$, $SiH_2(OiBu)[CH_2-Si(OEt)_3]$, $SiH_2(OSiMe_3)[CH_2-Si(OMe)_3]$, and $SiH_2(OSiMe_3)[CH_2-Si(OEt)_3]$.

Exemplary compounds wherein x=3, y=0, z=0, R'=Me or Et, a=1, b=2, and c=1 include $SiH(OMe)_2[CH_2-Si(OMe)_3]$, $SiH(OMe)_2[CH_2-Si(OEt)_3]$, $SiH(OEt)_2[CH_2-Si(OMe)_3]$, $SiH(OEt)_2[CH_2-Si(OEt)_3]$, $SiH(OiPr)_2[CH_2-Si(OMe)_3]$, $SiH(OiPr)_2[CH_2-Si(OEt)_3]$, $SiH(OnPr)_2[CH_2-Si(OMe)_3]$, $SiH(OnPr)_2[CH_2-Si(OEt)_3]$, $SiH(OnBu)_2[CH_2-Si(OMe)_3]$, $SiH(OnBu)_2[CH_2-Si(OEt)_3]$, $SiH(OtBu)_2[CH_2-Si(OMe)_3]$, $SiH(OtBu)_2[CH_2-Si(OEt)_3]$, $SiH(OiBu)_2[CH_2-Si(OMe)_3]$, $SiH(OiBu)_2[CH_2-Si(OEt)_3]$, $SiH(OSiMe_3)_2[CH_2-Si(OMe)_3]$, and $SiH(OSiMe_3)_2[CH_2-Si(OEt)_3]$.

Exemplary compounds wherein x=3, y=0, z=0, R'=Me or Et, a=1, b=3, and c=0 include $Si(OMe)_3[CH_2-Si(OMe)_3]$, $Si(OMe)_3[CH_2-Si(OEt)_3]$, $Si(OEt)_3[CH_2-Si(OMe)_3]$, $Si(OEt)_3[CH_2-Si(OEt)_3]$, $Si(OiPr)_3[CH_2-Si(OMe)_3]$, $Si(OiPr)_3[CH_2-Si(OEt)_3]$, $Si(OnPr)_3[CH_2-Si(OMe)_3]$, $Si(OnPr)_3[CH_2-Si(OEt)_3]$, $Si(OnBu)_3[CH_2-Si(OMe)_3]$, $Si(OnBu)_3[CH_2-Si(OEt)_3]$, $Si(OtBu)_3[CH_2-Si(OMe)_3]$, $Si(OtBu)_3[CH_2-Si(OEt)_3]$, $Si(OiBu)_3[CH_2-Si(OMe)_3]$, $Si(OiBu)_3[CH_2-Si(OEt)_3]$, $Si(OSiMe_3)_3[CH_2-Si(OMe)_3]$, and $Si(OSiMe_3)_3[CH_2-Si(OEt)_3]$.

In some embodiments, a=2, b=2, and c=0 to produce $Si(OR)_2[CH_2-Si(OR')_xH_yR_z]_2$, wherein x=0 to 3; y=0 to 1; z=0 to 3; x+y+z=3; each R is independently a C1 to C5 linear or branched alkyl group or a trimethylsilyl group; and each R' is independently a C1 to C5 linear or branched alkyl group.

Exemplary compounds wherein a=2, b=2, c=0, x=3, y=0, and z=0 include $Si(OMe)_2[CH_2-Si(OMe)_3]_2$, $Si(OMe)_2[CH_2-Si(OEt)_3]_2$, $Si(OMe)_2[CH_2-Si(OiPr)_3]_2$, $Si(OMe)_2[CH_2-Si(OnPr)_3]_2$, $Si(OMe)_2[CH_2-Si(OnBu)_3]_2$, $Si(OMe)_2[CH_2-Si(OtBu)_3]_2$, $Si(OMe)_2[CH_2-

Si(OiBu)₃]₂, Si(OEt)₂[CH₂—Si(OMe)₃]₂, Si(OEt)₂[CH₂—Si(OEt)₃]₂, Si(OEt)₂[CH₂—Si(OiPr)₃]₂, Si(OEt)₂[CH₂—Si(OnPr)₃]₂, Si(OEt)₂[CH₂—Si(OnBu)₃]₂, Si(OEt)₂[CH₂—Si(OtBu)₃]₂, Si(OEt)₂[CH₂—Si(OiBu)₃]₂, Si(OiPr)₂[CH₂—Si(OMe)₃]₂, Si(OiPr)₂[CH₂—Si(OEt)₃]₂, Si(OiPr)₂[CH₂—Si(OiPr)₃]₂, Si(OiPr)₂[CH₂—Si(OnPr)₃]₂, Si(OiPr)₂[CH₂—Si(OnBu)₃]₂, Si(OiPr)₂[CH₂—Si(OtBu)₃]₂, Si(OiPr)₂[CH₂—Si(OiBu)₃]₂, Si(OnPr)₂[CH₂—Si(OMe)₃]₂, Si(OnPr)₂[CH₂—Si(OEt)₃]₂, Si(OnPr)₂[CH₂—Si(OiPr)₃]₂, Si(OnPr)₂[CH₂—Si(OnPr)₃]₂, Si(OnPr)₂[CH₂—Si(OnBu)₃]₂, Si(OnPr)₂[CH₂—Si(OtBu)₃]₂, Si(OnPr)₂[CH₂—Si(OiBu)₃]₂, Si(OnBu)₂[CH₂—Si(OMe)₃]₂, Si(OnBu)₂[CH₂—Si(OEt)₃]₂, Si(OnBu)₂[CH₂—Si(OiPr)₃]₂, Si(OnBu)₂ [CH₂—Si(OnPr)₃]₂, Si(OnBu)₂[CH₂—Si(OnBu)₃]₂, Si(OnBu)₂[CH₂—Si(OtBu)₃]₂, Si(OnBu)₂[CH₂—Si(OiBu)₃]₂, Si(OtBu)₂[CH₂—Si(OMe)₃]₂, Si(OtBu)₂[CH₂—Si(OEt)₃]₂, Si(OtBu)₂[CH₂—Si(OiPr)₃]₂, Si(OtBu)₂[CH₂—Si(OnPr)₃]₂, Si(OtBu)₂[CH₂—Si(OnBu)₃]₂, Si(OtBu)₂[CH₂—Si(OtBu)₃]₂, Si(OtBu)₂[CH₂—Si(OiBu)₃]₂, Si(OiBu)₂[CH₂—Si(OMe)₃]₂, Si(OiBu)₂[CH₂—Si(OEt)₃]₂, Si(OiBu)₂[CH₂—Si(OiPr)₃]₂, Si(OiBu)₂[CH₂—Si(OnPr)₃]₂, Si(OiBu)₂[CH₂—Si(OnBu)₃]₂, Si(OiBu)₂[CH₂—Si(OtBu)₃]₂, Si(OiBu)₂[CH₂—Si(OiBu)₃]₂, Si(OSiMe₃)₂[CH₂—Si(OMe)₃]₂, Si(OSiMe₃)₂[CH₂—Si(OEt)₃]₂, Si(OSiMe₃)₂[CH₂—Si(OiPr)₃]₂, Si(OSiMe₃)₂[CH₂—Si(OnPr)₃]₂, Si(OSiMe₃)₂[CH₂—Si(OnBu)₃]₂, Si(OSiMe₃)₂[CH₂—Si(OiBu)₃]₂, and Si(OSiMe₃)₂[CH₂—Si(OtBu)₃]₂.

Exemplary compounds wherein a=2, b=2, c=0, x=2, y=1, and z=0 include Si(OMe)₂[CH₂—SiH(OMe)₂]₂, Si(OMe)₂[CH₂—SiH(OEt)₂]₂, Si(OMe)₂[CH₂—SiH(OiPr)₂]₂, Si(OMe)₂[CH₂—SiH(OnPr)₂]₂, Si(OMe)₂[CH₂—SiH(OnBu)₂]₂, Si(OMe)₂[CH₂—SiH(OtBu)₂]₂, Si(OMe)₂[CH₂—SiH(OiBu)₂]₂, Si(OEt)₂[CH₂—SiH(OMe)₂]₂, Si(OEt)₂[CH₂—SiH(OEt)₂]₂, Si(OEt)₂[CH₂—SiH(OiPr)₂]₂, Si(OEt)₂[CH₂—SiH(OnPr)₂]₂, Si(OEt)₂[CH₂—SiH(OnBu)₂]₂, Si(OEt)₂[CH₂—SiH(OtBu)₂]₂, Si(OEt)₂[CH₂—SiH(OiBu)₂]₂, Si(OiPr)₂[CH₂—SiH(OMe)₂]₂, Si(OiPr)₂[CH₂—SiH(OEt)₂]₂, Si(OiPr)₂[CH₂—SiH(OiPr)₂]₂, Si(OiPr)₂[CH₂—SiH(OnPr)₂]₂, Si(OiPr)₂[CH₂—SiH(OnBu)₂]₂, Si(OiPr)₂[CH₂—SiH(OtBu)₂]₂, Si(OiPr)₂[CH₂—SiH(OiBu)₂]₂, Si(OnPr)₂[CH₂—SiH(OMe)₂]₂, Si(OnPr)₂[CH₂—SiH(OEt)₂]₂, Si(OnPr)₂[CH₂—SiH(OiPr)₂]₂, Si(OnPr)₂[CH₂—SiH(OnPr)₂]₂, Si(OnPr)₂[CH₂—SiH(OnBu)₂]₂, Si(OnPr)₂[CH₂—SiH(OtBu)₂]₂, Si(OnPr)₂[CH₂—SiH(OiBu)₂]₂, Si(OnBu)₂[CH₂—SiH(OMe)₂]₂, Si(OnBu)₂[CH₂—SiH(OEt)₂]₂, Si(OnBu)₂[CH₂—SiH(OiPr)₂]₂, Si(OnBu)₂[CH₂—SiH(OnPr)₂]₂, Si(OnBu)₂[CH₂—SiH(OnBu)₂]₂, Si(OnBu)₂[CH₂—SiH(OiBu)₂]₂, Si(OnBu)₂[CH₂—SiH(OtBu)₂]₂, Si(OtBu)₂[CH₂—SiH(OMe)₂]₂, Si(OtBu)₂[CH₂—SiH(OEt)₂]₂, Si(OtBu)₂[CH₂—SiH(OiPr)₂]₂, Si(OtBu)₂[CH₂—SiH(OnPr)₂]₂, Si(OtBu)₂[CH₂—SiH(OnBu)₂]₂, Si(OtBu)₂[CH₂—SiH(OtBu)₂]₂, Si(OtBu)₂[CH₂—SiH(OiBu)₂]₂, Si(OiBu)₂[CH₂—SiH(OMe)₂]₂, Si(OiBu)₂[CH₂—SiH(OEt)₂]₂, Si(OiBu)₂[CH₂—SiH(OnPr)₂]₂, Si(OiBu)₂[CH₂—SiH(OiPr)₂]₂, Si(OiBu)₂[CH₂—SiH(OnBu)₂]₂, Si(OiBu)₂[CH₂—SiH(OtBu)₂]₂, Si(OiBu)₂[CH₂—SiH(OiBu)₂]₂, Si(OSiMe₃)₂[CH₂—SiH(OMe)₂]₂, Si(OSiMe₃)₂[CH₂—SiH(OEt)₂]₂, Si(OSiMe₃)₂[CH₂—SiH(OiPr)₂]₂, Si(OSiMe₃)₂[CH₂—SiH(OnPr)₂]₂, Si(OSiMe₃)₂[CH₂—SiH(OnBu)₂]₂, Si(OSiMe₃)₂[CH₂—SiH(OtBu)₂]₂, and Si(OSiMe₃)₂[CH₂—SiH(OiBu)₂]₂.

Exemplary compounds wherein a=2, b=2, c=0, x=2, y=0, and z=1 include Si(OMe)₂[CH₂—SiMe(OMe)₂]₂, Si(OMe)₂[CH₂—SiMe(OEt)₂]₂, Si(OMe)₂[CH₂—SiMe(OiPr)₂]₂, Si(OMe)₂[CH₂—SiMe(OnPr)₂]₂, Si(OMe)₂[CH₂—SiMe(OnBu)₂]₂, Si(OMe)₂[CH₂—SiMe(OtBu)₂]₂, Si(OMe)₂[CH₂—SiMe(OiBu)₂]₂, Si(OEt)₂[CH₂—SiMe(OMe)₂]₂, Si(OEt)₂[CH₂—SiMe(OEt)₂]₂, Si(OEt)₂[CH₂—SiMe(OiPr)₂]₂, Si(OEt)₂[CH₂—SiMe(OnPr)₂]₂, Si(OEt)₂[CH₂—SiMe(OnBu)₂]₂, Si(OEt)₂[CH₂—SiMe(OtBu)₂]₂, Si(OEt)₂[CH₂—SiMe(OiBu)₂]₂, Si(OiPr)₂[CH₂—SiMe(OMe)₂]₂, Si(OiPr)₂[CH₂—SiMe(OEt)₂]₂, Si(OiPr)₂[CH₂—SiMe(OiPr)₂]₂, Si(OiPr)₂[CH₂—SiMe(OnPr)₂]₂, Si(OiPr)₂[CH₂—SiMe(OnBu)₂]₂, Si(OiPr)₂[CH₂—SiMe(OtBu)₂]₂, Si(OiPr)₂[CH₂—SiMe(OiBu)₂]₂, Si(OnPr)₂[CH₂—SiMe(OMe)₂]₂, Si(OnPr)₂[CH₂—SiMe(OEt)₂]₂, Si(OnPr)₂[CH₂—SiMe(OiPr)₂]₂, Si(OnPr)₂[CH₂—SiMe(OnPr)₂]₂, Si(OnPr)₂[CH₂—SiMe(OnBu)₂]₂, Si(OnPr)₂[CH₂—SiMe(OtBu)₂]₂, Si(OnPr)₂[CH₂—SiMe(OiBu)₂]₂, Si(OnBu)₂[CH₂—SiMe(OMe)₂]₂, Si(OnBu)₂[CH₂—SiMe(OEt)₂]₂, Si(OnBu)₂[CH₂—SiMe(OiPr)₂]₂, Si(OnBu)₂[CH₂—SiMe(OnPr)₂]₂, Si(OnBu)₂[CH₂—SiMe(OnBu)₂]₂, Si(OnBu)₂[CH₂—SiMe(OiBu)₂]₂, Si(OnBu)₂[CH₂—SiMe(OtBu)₂]₂, Si(OtBu)₂[CH₂—SiMe(OMe)₂]₂, Si(OtBu)₂[CH₂—SiMe(OEt)₂]₂, Si(OtBu)₂[CH₂—SiMe(OiPr)₂]₂, Si(OtBu)₂[CH₂—SiMe(OnPr)₂]₂, Si(OtBu)₂[CH₂—SiMe(OnBu)₂]₂, Si(OtBu)₂[CH₂—SiMe(OtBu)₂]₂, Si(OtBu)₂[CH₂—SiMe(OiBu)₂]₂, Si(OiBu)₂[CH₂—SiMe(OMe)₂]₂, Si(OiBu)₂[CH₂—SiMe(OEt)₂]₂, Si(OiBu)₂[CH₂—SiMe(OnPr)₂]₂, Si(OiBu)₂[CH₂—SiMe(OiPr)₂]₂, Si(OiBu)₂[CH₂—SiMe(OnBu)₂]₂, Si(OiBu)₂[CH₂—SiMe(OtBu)₂]₂, Si(OiBu)₂[CH₂—SiMe(OiBu)₂]₂, Si(OSiMe₃)₂[CH₂—SiMe(OMe)₂]₂, Si(OSiMe₃)₂[CH₂—SiMe(OEt)₂]₂, Si(OSiMe₃)₂[CH₂—SiMe(OiPr)₂]₂, Si(OSiMe₃)₂[CH₂—SiMe(OnPr)₂]₂, Si(OSiMe₃)₂[CH₂—SiMe(OnBu)₂]₂, Si(OSiMe₃)₂[CH₂—SiMe(OtBu)₂]₂, and Si(OSiMe₃)₂[CH₂—SiMe(OiBu)₂]₂.

Exemplary compounds wherein a=2, b=2, c=0, x=1, y=1, and z=1 include Si(OMe)₂[CH₂—SiHMe(OMe)]₂, Si(OMe)₂[CH₂—SiHMe(OEt)]₂, Si(OMe)₂[CH₂—SiHMe(OiPr)]₂, Si(OMe)₂[CH₂—SiHMe(OnPr)]₂, Si(OMe)₂[CH₂—SiHMe(OnBu)]₂, Si(OMe)₂[CH₂—SiHMe(OtBu)]₂, Si(OMe)₂[CH₂—SiHMe(OiBu)]₂, Si(OEt)₂[CH₂—SiHMe(OMe)]₂, Si(OEt)₂[CH₂—SiHMe(OEt)]₂, Si(OEt)₂[CH₂—SiHMe(OiPr)]₂, Si(OEt)₂[CH₂—SiHMe(OnPr)]₂, Si(OEt)₂[CH₂—SiHMe(OnBu)]₂, Si(OEt)₂[CH₂—SiHMe(OtBu)]₂, Si(OEt)₂[CH₂—SiHMe(OiBu)]₂, Si(OiPr)₂[CH₂—SiHMe(OMe)]₂, Si(OiPr)₂[CH₂—SiHMe(OEt)]₂, Si(OiPr)₂[CH₂—SiHMe(OiPr)]₂, Si(OiPr)₂[CH₂—SiHMe(OnPr)]₂, Si(OiPr)₂[CH₂—SiHMe(OnBu)]₂, Si(OiPr)₂[CH₂—SiHMe(OtBu)]₂, Si(OiPr)₂[CH₂—SiHMe(OiBu)]₂, Si(OnPr)₂[CH₂—SiHMe(OMe)]₂, Si(OnPr)₂[CH₂—SiHMe(OEt)]₂, Si(OnPr)₂[CH₂—SiHMe(OiPr)]₂, Si(OnPr)₂[CH₂—SiHMe(OnPr)]₂, Si(OnPr)₂[CH₂—SiHMe(OnBu)]₂, Si(OnPr)₂[CH₂—SiHMe(OtBu)]₂, Si(OnPr)₂[CH₂—SiHMe(OiBu)]₂, Si(OnBu)₂[CH₂—SiHMe(OMe)]₂, Si(OnBu)₂[CH₂—SiHMe(OEt)]₂, Si(OnBu)₂[CH₂—SiHMe(OiPr)]₂, Si(OnBu)₂[CH₂—SiHMe(OnPr)]₂, Si(OnBu)₂[CH₂—SiHMe(OnBu)]₂, Si(OnBu)₂[CH₂—SiHMe(OiBu)]₂, Si(OnBu)₂[CH₂—SiHMe(OtBu)]₂, Si(OtBu)₂[CH₂—SiHMe(OMe)]₂, Si(OtBu)₂[CH₂—SiHMe(OEt)]₂, Si(OtBu)₂[CH₂—SiHMe(OiPr)]₂, Si(OtBu)₂[CH₂—SiHMe(OnPr)]₂, Si(OnBu)₂[CH₂—SiHMe(OnBu)]₂, Si(OtBu)₂[CH₂—SiHMe(OtBu)]₂, Si(OtBu)₂[CH₂—SiHMe(OiBu)]₂, Si(OiBu)₂[CH₂—SiHMe(OMe)]₂, Si(OiBu)₂[CH₂—SiHMe(OEt)]₂, Si(OiBu)₂[CH₂—SiHMe(OnPr)]2, Si(OiBu)₂[CH₂—SiHMe(OiPr)]₂, Si(OiBu)₂[CH₂—SiHMe(OnBu)]₂, Si(OiBu)₂ [CH₂—SiHMe(OtBu)]₂, Si(OiBu)₂[CH₂—SiHMe(OiBu)]₂, Si(OSiMe₃)₂[CH₂—SiHMe(OMe)]₂, Si(OSiMe₃)₂[CH₂—SiHMe(OEt)]₂, Si(OSiMe₃)₂[CH₂—SiHMe(OiPr)]₂, Si(OSiMe₃)₂[CH₂—SiHMe(OnPr)]₂, Si(OSiMe₃)₂[CH₂—SiHMe(OnBu)]₂, Si(OSiMe₃)₂[CH₂—SiHMe(OtBu)]₂, and Si(OSiMe₃)₂[CH₂—SiHMe(OiBu)]₂.

Exemplary compounds wherein a=2, b=2, c=0, x=1, y=0, and z=2 include Si(OMe)₂[CH₂—SiMe₂(OMe)]₂, Si(OMe)₂[CH₂—SiMe₂(OEt)]₂, Si(OMe)₂[CH₂—SiMe₂(OiPr)]₂, Si(OMe)$_2$[CH$_2$—SiMe$_2$(OnPr)]$_2$, Si(OMe)$_2$[CH$_2$—SiMe$_2$(OnBu)]$_2$, Si(OMe)$_2$[CH$_2$—SiMe$_2$(OtBu)]$_2$, Si(OMe)$_2$[CH$_2$—SiMe$_2$(OiBu)]$_2$, Si(OEt)$_2$[CH$_2$—SiMe$_2$(OMe)]$_2$, Si(OEt)$_2$[CH$_2$—SiMe$_2$(OEt)]$_2$, Si(OEt)$_2$[CH$_2$—SiMe$_2$(OiPr)]$_2$, Si(OEt)$_2$[CH$_2$—SiMe$_2$(OnPr)]$_2$, Si(OEt)$_2$[CH$_2$—SiMe$_2$(OnBu)]$_2$, Si(OEt)$_2$[CH$_2$—SiMe$_2$(OtBu)]$_2$, Si(OEt)$_2$[CH$_2$—SiMe$_2$(OiBu)]$_2$, Si(OiPr)$_2$[CH$_2$—SiMe$_2$(OMe)]$_2$, Si(OiPr)$_2$[CH$_2$—SiMe$_2$(OEt)]$_2$, Si(OiPr)$_2$[CH$_2$—SiMe$_2$(OiPr)]$_2$, Si(OiPr)$_2$[CH$_2$—SiMe$_2$(OnPr)]$_2$, Si(OiPr)$_2$[CH$_2$—SiMe$_2$(OnBu)]$_2$, Si(OiPr)$_2$[CH$_2$—SiMe$_2$(OtBu)]$_2$, Si(OnPr)$_2$[CH$_2$—SiMe$_2$(OiBu)]$_2$, Si(OnPr)$_2$[CH$_2$—SiMe$_2$(OMe)]$_2$, Si(OnPr)$_2$[CH$_2$—SiMe$_2$(OEt)]$_2$, Si(OnPr)$_2$[CH$_2$—SiMe$_2$(OiPr)]$_2$, Si(OnPr)$_2$[CH$_2$—SiMe$_2$(OnPr)]$_2$, Si(OnPr)$_2$[CH$_2$—SiMe$_2$(OnBu)]$_2$, Si(OnPr)$_2$[CH$_2$—SiMe$_2$(OtBu)]$_2$, Si(OnPr)$_2$[CH$_2$—SiMe$_2$(OiBu)]$_2$, Si(OnBu)$_2$[CH$_2$—SiMe$_2$(OMe)]$_2$, Si(OnBu)$_2$[CH$_2$—SiMe$_2$(OEt)]$_2$, Si(OnBu)$_2$[CH$_2$—SiMe$_2$(OiPr)]$_2$, Si(OnBu)$_2$[CH$_2$—SiMe$_2$(OnPr)]$_2$, Si(OnBu)$_2$[CH$_2$—SiMe$_2$(OnBu)]$_2$, Si(OnBu)$_2$[CH$_2$—SiMe$_2$(OiBu)]$_2$, Si(OnBu)$_2$[CH$_2$—SiMe$_2$(OtBu)]$_2$, Si(OtBu)$_2$[CH$_2$—SiMe$_2$(OMe)]$_2$, Si(OtBu)$_2$[CH$_2$—SiMe$_2$(OEt)]$_2$, Si(OtBu)$_2$[CH$_2$—SiMe$_2$(OiPr)]$_2$, Si(OtBu)$_2$[CH$_2$—SiMe$_2$(OnPr)]$_2$, Si(OtBu)$_2$[CH$_2$—SiMe$_2$(OnBu)]$_2$, Si(OtBu)$_2$[CH$_2$—SiMe$_2$(OtBu)]$_2$, Si(OtBu)$_2$[CH$_2$—SiMe$_2$(OiBu)]$_2$, Si(OiBu)$_2$[CH$_2$—SiMe$_2$(OMe)]$_2$, Si(OiBu)$_2$[CH$_2$—SiMe$_2$(OEt)]$_2$, Si(OiBu)$_2$[CH$_2$—SiMe$_2$(OnPr)]$_2$, Si(OiBu)$_2$[CH$_2$—SiMe$_2$(OiPr)]$_2$, Si(OiBu)$_2$[CH$_2$—SiMe$_2$(OnBu)]$_2$, Si(OiBu)$_2$[CH$_2$—SiMe$_2$(OtBu)]$_2$, Si(OiBu)$_2$[CH$_2$—SiMe$_2$(OiBu)]$_2$, Si(OSiMe$_3$)$_2$[CH$_2$—SiMe$_2$(OMe)]$_2$, Si(OSiMe$_3$)$_2$[CH$_2$—SiMe$_2$(OEt)]$_2$, Si(OSiMe$_3$)$_2$[CH$_2$—SiMe$_2$(OiPr)]$_2$, Si(OSiMe$_3$)$_2$[CH$_2$—SiMe$_2$(OnPr)]$_2$, Si(OSiMe$_3$)$_2$[CH$_2$—SiMe$_2$(OnBu)]$_2$, Si(OSiMe$_3$)$_2$[CH$_2$—SiMe$_2$(OtBu)]$_2$, and Si(OSiMe$_3$)$_2$[CH$_2$—SiMe$_2$(OiBu)]$_2$.

Exemplary compounds wherein a=2, b=2, c=0, x=0, y=1, and z=2 include Si(OMe)$_2$[CH$_2$—SiHMe$_2$]$_2$, Si(OMe)$_2$[CH$_2$—SiHEt$_2$]$_2$, Si(OMe)$_2$[CH$_2$—SiH(iPr)$_2$]$_2$, Si(OMe)$_2$[CH$_2$—SiH(nPr)$_2$]$_2$, Si(OMe)$_2$[CH$_2$—SiH(nBu)$_2$]$_2$, Si(OMe)$_2$[CH$_2$—SiH(OtBu)$_2$]$_2$, Si(OMe)$_2$[CH$_2$—SiH(iBu)$_2$]$_2$, Si(OMe)$_2$[CH$_2$—SiH(SiMe$_3$)$_2$]$_2$, Si(OEt)$_2$[CH$_2$—SiHMe$_2$]$_2$, Si(OEt)$_2$[CH$_2$—SiHEt$_2$]$_2$, Si(OEt)$_2$[CH$_2$—SiH(iPr)$_2$]$_2$, Si(OEt)$_2$[CH$_2$—SiH(nPr)$_2$]$_2$, Si(OEt)$_2$[CH$_2$—SiH(nBu)$_2$]$_2$, Si(OEt)$_2$[CH$_2$—SiH(OtBu)$_2$]$_2$, Si(OEt)$_2$[CH$_2$—SiH(iBu)$_2$]$_2$, Si(OEt)$_2$[CH$_2$—SiH(SiMe$_3$)$_2$]$_2$, Si(OiPr)$_2$[CH$_2$—SiHMe$_2$]$_2$, Si(OiPr)$_2$[CH$_2$—SiHEt$_2$]$_2$, Si(OiPr)$_2$[CH$_2$—SiH(iPr)$_2$]$_2$, Si(OiPr)$_2$[CH$_2$—SiH(nPr)$_2$]$_2$, Si(OiPr)$_2$[CH$_2$—SiH(nBu)$_2$]$_2$, Si(OiPr)$_2$[CH$_2$—SiH(OtBu)$_2$]$_2$, Si(OiPr)$_2$[CH$_2$—SiH(iBu)$_2$]$_2$, Si(OiPr)$_2$[CH$_2$—SiH(SiMe$_3$)$_2$]$_2$, Si(OnPr)$_2$[CH$_2$—SiHMe$_2$]$_2$, Si(OnPr)$_2$[CH$_2$—SiHEt$_2$]$_2$, Si(OnPr)$_2$[CH$_2$—SiH(iPr)$_2$]$_2$, Si(OnPr)$_2$[CH$_2$—SiH(nPr)$_2$]$_2$, Si(OnPr)$_2$[CH$_2$—SiH(nBu)$_2$]$_2$, Si(OnPr)$_2$[CH$_2$—SiH(OtBu)$_2$]$_2$, Si(OnPr)$_2$[CH$_2$—SiH(iBu)$_2$]$_2$, Si(OnPr)$_2$[CH$_2$—SiH(SiMe$_3$)$_2$]$_2$, Si(OnBu)$_2$[CH$_2$—SiHMe$_2$]$_2$, Si(OnBu)$_2$[CH$_2$—SiHEt$_2$]$_2$, Si(OnBu)$_2$[CH$_2$—SiH(iPr)$_2$]$_2$, Si(OnBu)$_2$[CH$_2$—SiH(nPr)$_2$]$_2$, Si(OnBu)$_2$[CH$_2$—SiH(nBu)$_2$]$_2$, Si(OnBu)$_2$[CH$_2$—SiH(OtBu)$_2$]$_2$, Si(OnBu)$_2$[CH$_2$—SiH(iBu)$_2$]$_2$, Si(OnBu)$_2$[CH$_2$—SiH(SiMe$_3$)$_2$]$_2$, Si(OiBu)$_2$[CH$_2$—SiHMe$_2$]2, Si(OiBu)$_2$[CH$_2$—SiHEt$_2$]$_2$, Si(OiBu)$_2$[CH$_2$—SiH(iPr)$_2$]$_2$, Si(OiBu)$_2$[CH$_2$—SiH(nPr)$_2$]$_2$, Si(OiBu)$_2$[CH$_2$—SiH(nBu)$_2$]$_2$, Si(OiBu)$_2$[CH$_2$—SiH(OtBu)$_2$]$_2$, Si(OiBu)$_2$[CH$_2$—SiH(iBu)$_2$]$_2$, Si(OiBu)$_2$[CH$_2$—SiH(SiMe$_3$)$_2$]$_2$, Si(OtBu)$_2$[CH$_2$—SiHMe$_2$]$_2$, Si(OtBu)$_2$[CH$_2$—SiHEt$_2$]$_2$, Si(OtBu)$_2$[CH$_2$—SiH(iPr)$_2$]$_2$, Si(OtBu)$_2$[CH$_2$—SiH(nPr)$_2$]$_2$, Si(OtBu)$_2$[CH$_2$—SiH(nBu)$_2$]$_2$, Si(OtBu)$_2$[CH$_2$—SiH(OtBu)$_2$]$_2$, Si(OtBu)$_2$[CH$_2$—SiH(iBu)$_2$]$_2$, Si(OtBu)$_2$[CH$_2$—SiH(SiMe$_3$)$_2$]$_2$, Si(OSiMe$_3$)$_2$[CH$_2$—SiHMe$_2$]$_2$, Si(OSiMe$_3$)$_2$[CH$_2$—SiHEt$_2$]$_2$, Si(OSiMe$_3$)$_2$[CH$_2$—SiH(iPr)$_2$]$_2$, Si(OSiMe$_3$)$_2$[CH$_2$—SiH(nPr)$_2$]$_2$, Si(OSiMe$_3$)$_2$[CH$_2$—SiH(nBu)$_2$]$_2$, Si(OSiMe$_3$)$_2$[CH$_2$—SiH(OtBu)$_2$]$_2$, Si(OSiMe$_3$)$_2$[CH$_2$—SiH(iBu)$_2$]$_2$, and Si(OSiMe$_3$)$_2$[CH$_2$—SiH(SiMe$_3$)$_2$]$_2$.

Exemplary compounds wherein a=2, b=2, c=0, x=0, y=0, and z=3 include Si(OMe)$_2$[CH$_2$—SiMe$_3$]$_2$, Si(OMe)$_2$[CH$_2$—SiEt$_3$]$_2$, Si(OMe)$_2$[CH$_2$—Si(iPr)$_3$]$_2$, Si(OMe)$_2$[CH$_2$—Si(nPr)$_3$]$_2$, Si(OMe)$_2$[CH$_2$—Si(nBu)$_3$]$_2$, Si(OMe)$_2$[CH$_2$—Si(OtBu)$_3$]$_2$, Si(OMe)$_2$[CH$_2$—Si(iBu)$_3$]$_2$, Si(OMe)$_2$[CH$_2$—Si(SiMe$_3$)$_3$]$_2$, Si(OEt)$_2$[CH$_2$—SiMe$_3$]$_2$, Si(OEt)$_2$[CH$_2$—SiEt$_3$]$_2$, Si(OEt)$_2$[CH$_2$—Si(iPr)$_3$]$_2$, Si(OEt)$_2$[CH$_2$—SiH(nPr)$_3$]$_2$, Si(OEt)$_2$[CH$_2$—Si(nBu)$_3$]$_2$, Si(OEt)$_2$[CH$_2$—Si(OtBu)$_3$]$_2$, Si(OEt)$_2$[CH$_2$—Si(iBu)$_3$]$_2$, Si(OEt)$_2$[CH$_2$—Si(SiMe$_3$)$_3$]$_2$, Si(OiPr)$_2$[CH$_2$—SiMe$_3$]$_2$, Si(OiPr)$_2$[CH$_2$—SiEt$_3$]$_2$, Si(OiPr)$_2$[CH$_2$—Si(iPr)$_3$]$_2$, Si(OiPr)$_2$[CH$_2$—Si(nPr)$_3$]$_2$, Si(OiPr)$_2$[CH$_2$—Si(nBu)$_3$]$_2$, Si(OiPr)$_2$[CH$_2$—Si(OtBu)$_3$]$_2$, Si(OiPr)$_2$[CH$_2$—Si(iBu)$_3$]$_2$, Si(OiPr)$_2$[CH$_2$—Si(SiMe$_3$)$_3$]$_2$, Si(OnPr)$_2$[CH$_2$—SiMe$_3$]$_2$, Si(OnPr)$_2$[CH$_2$—SiEt$_3$]$_2$, Si(OnPr)$_2$[CH$_2$—Si(iPr)$_3$]$_2$, Si(OnPr)$_2$[CH$_2$—Si(nPr)$_3$]$_2$, Si(OnPr)$_2$[CH$_2$—Si(nBu)$_3$]$_2$, Si(OnPr)$_2$[CH$_2$—Si(OtBu)$_3$]$_2$, Si(OnPr)$_2$[CH$_2$—Si(iBu)$_3$]$_2$, Si(OnPr)$_2$[CH$_2$—Si(SiMe$_3$)$_3$]$_2$, Si(OnBu)$_2$[CH$_2$—SiMe$_3$]$_2$, Si(OnBu)$_2$[CH$_2$—SiEt$_3$]$_2$, Si(OnBu)$_2$[CH$_2$—Si(iPr)$_3$]$_2$, Si(OnBu)$_2$[CH$_2$—Si(nPr)$_3$]$_2$, Si(OiBu)$_2$[CH$_2$—Si(OtBu)$_3$]$_2$, Si(OnBu)$_2$[CH$_2$—Si(OtBu)$_3$]$_2$, Si(OnBu)$_2$[CH$_2$—Si(iBu)$_3$]$_2$, Si(OnBu)$_2$[CH$_2$—Si(SiMe$_3$)$_3$]$_2$, Si(OiBu)$_2$[CH$_2$—SiMe$_3$]$_2$, Si(OiBu)$_2$[CH$_2$—SiEt$_3$]$_2$, Si(OiBu)$_2$[CH$_2$—Si(iPr)$_3$]$_2$, Si(OiBu)$_2$[CH$_2$—Si(nPr)$_3$]$_2$, Si(OiBu)$_2$[CH$_2$—Si(nBu)$_3$]$_2$, Si(OiBu)$_2$[CH$_2$—SiH(OtBu)$_2$]$_2$, Si(OiBu)$_2$[CH$_2$—Si(iBu)$_3$]$_2$, Si(OiBu)$_2$[CH$_2$—Si(SiMe$_3$)$_3$]$_2$, Si(OtBu)$_2$[CH$_2$—SiMe$_3$]$_2$, Si(OtBu)$_2$[CH$_2$—SiEt$_3$]$_2$, Si(OtBu)$_2$[CH$_2$—Si(iPr)$_3$]$_2$, Si(OtBu)$_2$[CH$_2$—Si(nPr)$_3$]$_2$, Si(OtBu)$_2$[CH$_2$—Si(nBu)$_3$]$_2$, Si(OtBu)$_2$[CH$_2$—Si(OtBu)$_3$]$_2$, Si(OtBu)$_2$[CH$_2$—Si(iBu)$_3$]$_2$, Si(OtBu)$_2$[CH$_2$—Si(SiMe$_3$)$_3$]$_2$, Si(OSiMe$_3$)$_2$[CH$_2$—SiMe$_3$]$_2$, Si(OSiMe$_3$)$_2$[CH$_2$—SiEt$_3$]$_2$, Si(OSiMe$_3$)$_2$[CH$_2$—Si(iPr)$_3$]$_2$, Si(OSiMe$_3$)$_2$[CH$_2$—Si(nPr)$_3$]$_2$, Si(OSiMe$_3$)$_2$[CH$_2$—Si(nBu)$_3$]$_2$, Si(OSiMe$_3$)$_2$[CH$_2$—Si(OtBu)$_3$]$_2$, Si(OSiMe$_3$)$_2$[CH$_2$—Si(iBu)$_3$]$_2$, and Si(OSiMe$_3$)$_2$[CH$_2$—Si(SiMe$_3$)$_3$]$_2$.

In some embodiments, y=1 and b=0 to produce Si(H)$_c$[CH$_2$—Si(OR')$_x$HR$_{2-x}$]$_a$, wherein a=1 to 3; c=0 to 2; a+c=4; x=0 to 2; each R is independently a C1 to C5 linear or branched alkyl group or a trimethylsilyl group; and each R' is independently a C1 to C5 linear or branched alkyl group.

Exemplary compounds wherein y=1, b=0, a=3, c=1, x=2, and z=0 include SiH[CH$_2$—SiH(OMe)$_2$]$_3$, SiH[CH$_2$—SiH(OEt)$_2$]$_3$, SiH[CH$_2$—SiH(OiPr)$_2$]$_3$, SiH[CH$_2$—SiH(OnPr)$_2$]$_3$, SiH[CH$_2$—SiH(OnBu)$_2$]$_3$, SiH[CH$_2$—SiH(OtBu)$_2$]$_3$, and SiH[CH$_2$—SiH(OiBu)$_2$]$_3$.

Exemplary compounds wherein y=1, b=0, a=3, c=1, x=0, and z=2 include SiH[CH$_2$—SiH(Me)$_2$]$_3$, SiH[CH$_2$—SiH(Et)$_2$]$_3$, SiH[CH$_2$—SiH(iPr)$_2$]$_3$, SiH[CH$_2$—SiH(nPr)$_2$]$_3$, SiH[CH$_2$—SiH(nBu)$_2$]$_3$, SiH[CH$_2$—SiH(tBu)$_2$]$_3$, SiH[CH$_2$—SiH(iBu)$_2$]$_3$, and SiH[CH$_2$—SiH(SiMe$_3$)$_2$]$_3$.

Exemplary compounds wherein y=1, b=0, a=3, c=1, x=1, and z=1 include SiH[CH$_2$—SiH(Me)(OMe)]$_3$, SiH[CH$_2$—SiH(Me)(OEt)]$_3$, SiH[CH$_2$—SiH(Me)(OiPr)]$_3$, SiH[CH$_2$—SiH(Me)(OnPr)]$_3$, SiH[CH$_2$—SiH(Me)(OnBu)]$_3$, SiH[CH$_2$—SiH(Me)(OtBu)]$_3$, SiH[CH$_2$—SiH(Me)(OiBu)]$_3$, SiH[CH$_2$—SiH(Et)(OMe)]$_3$, SiH[CH$_2$—SiH(Et)(OEt)]$_3$, SiH[CH$_2$—SiH(Et)(OiPr)]$_3$, SiH[CH$_2$—SiH(Et)(OnPr)]$_3$, SiH[CH$_2$—SiH(Et)(OnBu)]$_3$, SiH[CH$_2$—SiH(Et)(OtBu)]$_3$, SiH[CH$_2$—SiH(Et)(OiBu)]$_3$, SiH[CH$_2$—SiH(Pr)(OMe)]$_3$, SiH[CH$_2$—SiH(iPr)(OEt)]$_3$, SiH[CH$_2$—SiH(iPr)(OiPr)]$_3$, SiH[CH$_2$—SiH(iPr)(OnPr)]$_3$, SiH[CH$_2$—SiH(iPr)(OnBu)]$_3$, SiH[CH$_2$—SiH(iPr)(OtBu)]$_3$, SiH[CH$_2$—SiH(iPr)(OiBu)]$_3$, SiH[CH$_2$—SiH(nPr)(OMe)]$_3$, SiH[CH$_2$—SiH(nPr)(OEt)]$_3$, SiH[CH$_2$—SiH(nPr)(OiPr)]$_3$, SiH[CH$_2$—SiH(nPr)(OnPr)]$_3$, SiH[CH$_2$—SiH(nPr)(OnBu)]$_3$, SiH

[CH$_2$—SiH(nPr)(OtBu)]$_3$, SiH[CH$_2$—SiH(nPr)(OiBu)]$_3$, SiH[CH$_2$—SiH(nBu)(OMe)]$_3$, SiH[CH$_2$—SiH(nBu)(OEt)]$_3$, SiH[CH$_2$—SiH(nBu)(OiPr)]$_3$, SiH[CH$_2$—SiH(nBu)(OnPr)]$_3$, SiH[CH$_2$—SiH(nBu)(OnBu)]$_3$, SiH[CH$_2$—SiH(nBu)(OtBu)]$_3$, SiH[CH$_2$—SiH(nBu)(OiBu)]$_3$, SiH[CH$_2$—SiH(tBu)(OMe)]$_3$, SiH[CH$_2$—SiH(tBu)(OEt)]$_3$, SiH[CH$_2$—SiH(tBu)(OiPr)]$_3$, SiH[CH$_2$—SiH(tBu)(OnPr)]$_3$, SiH[CH$_2$—SiH(tBu)(OnBu)]$_3$, SiH[CH$_2$—SiH(tBu)(OtBu)]$_3$, SiH[CH$_2$—SiH(tBu)(OiBu)]$_3$, SiH[CH$_2$—SiH(iBu)(OMe)]$_3$, SiH[CH$_2$—SiH(iBu)(OEt)]$_3$, SiH[CH$_2$—SiH(iBu)(OiPr)]$_3$, SiH[CH$_2$—SiH(iBu)(OnPr)]$_3$, SiH[CH$_2$—SiH(iBu)(OnBu)]$_3$, SiH[CH$_2$—SiH(iBu)(OtBu)]$_3$, SiH[CH$_2$—SiH(iBu)(OiBu)]$_3$, SiH[CH$_2$—SiH(SiMe$_3$)(OMe)]$_3$, SiH[CH$_2$—SiH(SiMe$_3$)(OEt)]$_3$, SiH[CH$_2$—SiH(SiMe$_3$)(OiPr)]$_3$, SiH[CH$_2$—SiH(SiMe$_3$)(OnPr)]$_3$, SiH[CH$_2$—SiH(SiMe$_3$)(OnBu)]$_3$, SiH[CH$_2$—SiH(SiMe$_3$)(OtBu)]$_3$, and SiH[CH$_2$—SiH(SiMe$_3$)(OiBu)]$_3$.

Exemplary compounds wherein y=1, b=0, a=2, c=2, x=2, and z=0 include SiH$_2$[CH$_2$—SiH(OMe)$_2$]$_2$, SiH$_2$[CH$_2$—SiH(OEt)$_2$]$_2$, SiH$_2$[CH$_2$—SiH(OiPr)$_2$]$_2$, SiH$_2$[CH$_2$—SiH(OnPr)$_2$]$_2$, SiH$_2$[CH$_2$—SiH(OnBu)$_2$]$_2$, SiH$_2$[CH$_2$—SiH(OtBu)$_2$]$_2$, and SiH$_2$[CH$_2$—SiH(OiBu)$_2$]$_2$.

Exemplary compounds wherein y=1, b=0, a=2, c=2, x=0, and z=2 include SiH$_2$[CH$_2$—SiH(Me)$_2$]$_2$, SiH$_2$[CH$_2$—SiH(Et)$_2$]$_2$, SiH$_2$[CH$_2$—SiH(iPr)$_2$]$_2$, SiH$_2$[CH$_2$—SiH(nPr)$_2$]$_2$, SiH$_2$[CH$_2$—SiH(nBu)$_2$]$_2$, SiH$_2$[CH$_2$—SiH(tBu)$_2$]$_2$, SiH$_2$[CH$_2$—SiH(iBu)$_2$]$_2$, and SiH$_2$[CH$_2$—SiH(SiMe$_3$)$_2$]$_2$.

Exemplary compounds wherein y=1, b=0, a=2, c=2, x=1, and z=1 include SiH$_2$[CH$_2$—SiH(Me)(OMe)]$_2$, SiH$_2$[CH$_2$—SiH(Me)(OEt)]$_2$, SiH$_2$[CH$_2$—SiH(Me)(OiPr)]$_2$, SiH$_2$[CH$_2$—SiH(Me)(OnPr)]$_2$, SiH$_2$[CH$_2$—SiH(Me)(OnBu)]$_2$, SiH$_2$[CH$_2$—SiH(Me)(OiBu)]$_2$, SiH$_2$[CH$_2$—SiH(Me)(OtBu)]$_2$, SiH$_2$[CH$_2$—SiH(Et)(OMe)]$_2$, SiH$_2$[CH$_2$—SiH(Et)(OEt)]$_2$, SiH$_2$[CH$_2$—SiH(Et)(OiPr)]$_2$, SiH$_2$[CH$_2$—SiH(Et)(OnPr)]$_2$, SiH$_2$[CH$_2$—SiH(Et)(OnBu)]$_2$, SiH$_2$[CH$_2$—SiH(Et)(OtBu)]$_2$, SiH$_2$[CH$_2$—SiH(Et)(OiBu)]$_2$, SiH$_2$[CH$_2$—SiH(iPr)(OMe)]$_2$, SiH$_2$[CH$_2$—SiH(iPr)(OEt)]$_2$, SiH$_2$[CH$_2$—SiH(iPr)(OiPr)]$_2$, SiH$_2$[CH$_2$—SiH(iPr)(OnPr)]$_2$, SiH$_2$[CH$_2$—SiH(iPr)(OnBu)]$_2$, SiH$_2$[CH$_2$—SiH(iPr)(OtBu)]$_2$, SiH$_2$[CH$_2$—SiH(iPr)(OiBu)]$_2$, SiH$_2$[CH$_2$—SiH(nPr)(OMe)]$_2$, SiH$_2$[CH$_2$—SiH(nPr)(OEt)]$_2$, SiH$_2$[CH$_2$—SiH(nPr)(OnPr)]$_2$, SiH$_2$[CH$_2$—SiH(nPr)(OiPr)]$_2$, SiH$_2$[CH$_2$—SiH(nPr)(OnBu)]$_2$, SiH$_2$[CH$_2$—SiH(nPr)(OtBu)]$_2$, SiH$_2$[CH$_2$—SiH(nPr)(OiBu)]$_2$, SiH$_2$[CH$_2$—SiH(nBu)(OMe)]$_2$, SiH$_2$[CH$_2$—SiH(nBu)(OEt)]$_2$, SiH$_2$[CH$_2$—SiH(nBu)(OnPr)]$_2$, SiH$_2$[CH$_2$—SiH(nBu)(OiPr)]$_2$, SiH$_2$[CH$_2$—SiH(nBu)(OnBu)]$_2$, SiH$_2$[CH$_2$—SiH(nBu)(OtBu)]$_2$, SiH$_2$[CH$_2$—SiH(nBu)(OiBu)]$_2$, SiH$_2$[CH$_2$—SiH(tBu)(OMe)]$_2$, SiH$_2$[CH$_2$—SiH(tBu)(OEt)]$_2$, SiH$_2$[CH$_2$—SiH(tBu)(OnPr)]$_2$, SiH$_2$[CH$_2$—SiH(tBu)(OiPr)]$_2$, SiH$_2$[CH$_2$—SiH(tBu)(OnBu)]$_2$, SiH$_2$[CH$_2$—SiH(tBu)(OtBu)]$_2$, SiH$_2$[CH$_2$—SiH(tBu)(OiBu)]$_2$, SiH$_2$[CH$_2$—SiH(iBu)(OMe)]$_2$, SiH$_2$[CH$_2$—SiH(iBu)(OEt)]$_2$, SiH$_2$[CH$_2$—SiH(iBu)(OnPr)]$_2$, SiH$_2$[CH$_2$—SiH(iBu)(OiPr)]$_2$, SiH$_2$[CH$_2$—SiH(iBu)(OnBu)]$_2$, SiH$_2$[CH$_2$—SiH(iBu)(OtBu)]$_2$, SiH$_2$[CH$_2$—SiH(iBu)(OiBu)]$_2$, SiH$_2$[CH$_2$—SiH(SiMe$_3$)(OMe)]$_2$, SiH$_2$[CH$_2$—SiH(SiMe$_3$)(OEt)]$_2$, SiH$_2$[CH$_2$—SiH(SiMe$_3$)(OnPr)]$_2$, SiH$_2$[CH$_2$—SiH(SiMe$_3$)(OiPr)]$_2$, SiH$_2$[CH$_2$—SiH(SiMe$_3$)(OnBu)]$_2$, SiH$_2$[CH$_2$—SiH(SiMe$_3$)(OtBu)]$_2$, and SiH$_2$[CH$_2$—SiH(SiMe$_3$)(OiBu)]$_2$.

In some embodiments, z=0 and c=2 to produce Si(OR)$_{2-a}$H$_2$[CH$_2$—Si(OR)$_{3-y}$H$_y$]$_a$, wherein a=1 to 2; y=0 to 1; each R is independently a C1 to C5 linear or branched alkyl group or a trimethylsilyl group; and each R' is independently a C1 to C5 linear or branched alkyl group.

Exemplary compounds wherein z=0, c=2, a=2, and y=1 include SiH$_2$[CH$_2$—SiH(OMe)$_2$]$_2$, SiH$_2$[CH$_2$—SiH(OEt)$_2$]$_2$, SiH$_2$[CH$_2$—SiH(OiPr)$_2$]$_2$, SiH$_2$[CH$_2$—SiH(OnPr)$_2$]$_2$, SiH$_2$[CH$_2$—SiH(OnBu)$_2$]$_2$, SiH$_2$[CH$_2$—SiH(OtBu)$_2$]$_2$, SiH$_2$[CH$_2$—SiH(OiBu)$_2$]$_2$.

Exemplary compounds wherein z=0, c=2, a=2, and y=0 include SiH$_2$[CH$_2$—Si(OMe)$_3$]$_2$, SiH$_2$[CH$_2$—Si(OEt)$_3$]$_2$, SiH$_2$[CH$_2$—Si(OiPr)$_3$]$_2$, SiH$_2$[CH$_2$—Si(OnPr)$_3$]$_2$, SiH$_2$[CH$_2$—Si(OnBu)$_3$]$_2$, SiH$_2$[CH$_2$—Si(OtBu)$_3$]$_2$, SiH$_2$[CH$_2$—Si(OiBu)$_3$]$_2$.

Exemplary compounds wherein z=0, c=2, a=1, and y=1 include Si(OMe)H$_2$[CH$_2$—SiH(OMe)$_2$], Si(OMe)H$_2$[CH$_2$—SiH(OEt)$_2$], Si(OMe)H$_2$[CH$_2$—SiH(OiPr)$_2$], Si(OMe)H$_2$[CH$_2$—SiH(OnPr)$_2$], Si(OMe)H$_2$[CH$_2$—SiH(OnBu)$_2$], Si(OMe)H$_2$[CH$_2$—SiH(OtBu)$_2$], Si(OMe)H$_2$[CH$_2$—SiH(OiBu)$_2$], Si(OEt)H$_2$[CH$_2$—SiH(OMe)$_2$], Si(OEt)H$_2$[CH$_2$—SiH(OEt)$_2$], Si(OEt)H$_2$[CH$_2$—SiH(OiPr)$_2$], Si(OEt)H$_2$[CH$_2$—SiH(OnPr)$_2$], Si(OEt)H$_2$[CH$_2$—SiH(OnBu)$_2$], Si(OEt)H$_2$[CH$_2$—SiH(OtBu)$_2$], Si(OEt)H$_2$[CH$_2$—SiH(OiBu)$_2$], Si(OiPr)H$_2$[CH$_2$—SiH(OMe)$_2$], Si(OiPr)H$_2$[CH$_2$—SiH(OEt)$_2$], Si(OiPr)H$_2$[CH$_2$—SiH(OiPr)$_2$], Si(OiPr)H$_2$[CH$_2$—SiH(OnPr)$_2$], Si(OiPr)H$_2$[CH$_2$—SiH(OnBu)$_2$], Si(OiPr)H$_2$[CH$_2$—SiH(OtBu)$_2$], Si(OiPr)H$_2$[CH$_2$—SiH(OiBu)$_2$], Si(OnPr)H$_2$[CH$_2$—SiH(OMe)$_2$], Si(OnPr)H$_2$[CH$_2$—SiH(OEt)$_2$], Si(OnPr)H$_2$[CH$_2$—SiH(OiPr)$_2$], Si(OnPr)H$_2$[CH$_2$—SiH(OnPr)$_2$], Si(OnPr)H$_2$[CH$_2$—SiH(OnBu)$_2$], Si(OnPr)H$_2$[CH$_2$—SiH(OtBu)$_2$], Si(OnPr)H$_2$[CH$_2$—SiH(OiBu)$_2$], Si(OnBu)H$_2$[CH$_2$—SiH(OMe)$_2$], Si(OnBu)H$_2$[CH$_2$—SiH(OEt)$_2$], Si(OnBu)H$_2$[CH$_2$—SiH(OiPr)$_2$], Si(OnBu)H$_2$[CH$_2$—SiH(OnPr)$_2$], Si(OnBu)H$_2$[CH$_2$—SiH(OnBu)$_2$], Si(OnBu)H$_2$[CH$_2$—SiH(OtBu)$_2$], Si(OnBu)H$_2$[CH$_2$—SiH(OiBu)$_2$], Si(OtBu)H$_2$[CH$_2$—SiH(OMe)$_2$], Si(OtBu)H$_2$[CH$_2$—SiH(OEt)$_2$], Si(OtBu)H$_2$[CH$_2$—SiH(OiPr)$_2$], Si(OtBu)H$_2$[CH$_2$—SiH(OnPr)$_2$], Si(OtBu)H$_2$[CH$_2$—SiH(OnBu)$_2$], Si(OtBu)H$_2$[CH$_2$—SiH(OtBu)$_2$], Si(OtBu)H$_2$[CH$_2$—SiH(OiBu)$_2$], Si(OiBu)H$_2$[CH$_2$—SiH(OMe)$_2$], Si(OiBu)H$_2$[CH$_2$—SiH(OEt)$_2$], Si(OiBu)H$_2$[CH$_2$—SiH(OiPr)$_2$], Si(OiBu)H$_2$[CH$_2$—SiH(OnPr)$_2$], Si(OiBu)H$_2$[CH$_2$—SiH(OnBu)$_2$], Si(OiBu)H$_2$[CH$_2$—SiH(OtBu)$_2$], Si(OiBu)H$_2$[CH$_2$—SiH(OiBu)$_2$], Si(OSiMe$_3$)H$_2$[CH$_2$—SiH(OMe)$_2$], Si(OSiMe$_3$)H$_2$[CH$_2$—SiH(OEt)$_2$], Si(OSiMe$_3$)H$_2$[CH$_2$—SiH(OiPr)$_2$], Si(OSiMe$_3$)H$_2$[CH$_2$—SiH(OnPr)$_2$], Si(OSiMe$_3$)H$_2$[CH$_2$—SiH(OnBu)$_2$], Si(OSiMe$_3$)H$_2$[CH$_2$—SiH(OtBu)$_2$], Si(OSiMe$_3$)H$_2$[CH$_2$—SiH(OiBu)$_2$].

Exemplary compounds wherein z=0, c=2, a=1, and y=0 include Si(OMe)H$_2$[CH$_2$—Si(OMe)$_3$], Si(OMe)H$_2$[CH$_2$—Si(OEt)$_3$], Si(OMe)H$_2$[CH$_2$—Si(OiPr)$_3$], Si(OMe)H$_2$[CH$_2$—Si(OnPr)$_3$], Si(OMe)H$_2$[CH$_2$—Si(OnBu)$_3$], Si(OMe)H$_2$[CH$_2$—Si(OtBu)$_3$], Si(OMe)H$_2$[CH$_2$—Si(OiBu)$_3$], Si(OEt)H$_2$[CH$_2$—Si(OMe)$_3$], Si(OEt)H$_2$[CH$_2$—Si(OEt)$_3$], Si(OEt)H$_2$[CH$_2$—Si(OiPr)$_3$], Si(OEt)H$_2$[CH$_2$—Si(OnPr)$_3$], Si(OEt)H$_2$[CH$_2$—Si(OnBu)$_3$], Si(OEt)H$_2$[CH$_2$—Si(OtBu)$_3$], Si(OEt)H$_2$[CH$_2$—Si(OiBu)$_3$], Si(OiPr)H$_2$[CH$_2$—Si(OMe)$_3$], Si(OiPr)H$_2$[CH$_2$—Si(OEt)$_3$], Si(OiPr)H$_2$[CH$_2$—Si(OiPr)$_3$], Si(OiPr)H$_2$[CH$_2$—Si(OnPr)$_3$], Si(OiPr)H$_2$[CH$_2$—Si(OnBu)$_3$], Si(OiPr)H$_2$[CH$_2$—Si(OtBu)$_3$], Si(OiPr)H$_2$[CH$_2$—Si(OiBu)$_3$], Si(OnPr)H$_2$[CH$_2$—Si(OMe)$_3$], Si(OnPr)H$_2$[CH$_2$—Si(OEt)$_3$], Si(OnPr)H$_2$[CH$_2$—Si(OiPr)$_3$], Si(OnPr)H$_2$[CH$_2$—Si(OnPr)$_3$], Si(OnPr)H$_2$[CH$_2$—Si(OnBu)$_3$], Si(OnPr)H$_2$[CH$_2$—Si(OtBu)$_3$], Si(OnPr)H$_2$[CH$_2$—Si(OiBu)$_3$], Si(OnBu)H$_2$[CH$_2$—Si(OMe)$_3$], Si(OnBu)H$_2$[CH$_2$—Si(OEt)$_3$], Si(OnBu)H$_2$[CH$_2$—Si(OiPr)$_3$], Si(OnBu)H$_2$[CH$_2$—Si(OnPr)$_3$], Si(OnBu)H$_2$[CH$_2$—Si(OnBu)$_3$], Si(OnBu)H$_2$[CH$_2$—Si(OtBu)$_3$], Si(OnBu)H$_2$[CH$_2$—Si(OiBu)$_3$], Si(OtBu)H$_2$[CH$_2$—Si(OMe)$_3$], Si(OtBu)H$_2$[CH$_2$—Si(OEt)$_3$], Si(OtBu)H$_2$[CH$_2$—Si(OiPr)$_3$], Si(OtBu)H$_2$[CH$_2$—Si(OnPr)$_3$], Si(OtBu)H$_2$[CH$_2$—Si(OnBu)$_3$], Si(OtBu)H$_2$[CH$_2$—Si(OtBu)$_3$], Si(OtBu)H$_2$[CH$_2$—Si(OiBu)$_3$], Si(OiBu)H$_2$[CH$_2$—Si(OMe)$_3$], Si(OiBu)H$_2$[CH$_2$—Si(OEt)$_3$], Si(OiBu)H$_2$[CH$_2$—Si(OiPr)$_3$], Si(OiBu)H$_2$[CH$_2$—Si(OnPr)$_3$], Si(OiBu)H$_2$[CH$_2$—Si(OnBu)$_3$], Si(OiBu)H$_2$[CH$_2$—Si(OtBu)$_3$], Si(OiBu)H$_2$[CH$_2$—Si(OiBu)$_3$], Si(OSiMe$_3$)H$_2$[CH$_2$—Si(OMe)$_3$], Si(OSiMe$_3$)H$_2$[CH$_2$—Si(OEt)$_3$], Si(OSiMe$_3$)H$_2$[CH$_2$—Si(OiPr)$_3$], Si(OSiMe$_3$)H$_2$[CH$_2$—Si(OnPr)$_3$], Si(OSiMe$_3$)H$_2$[CH$_2$—Si(OnBu)$_3$], Si(OSiMe$_3$)H$_2$[CH$_2$—Si(OtBu)$_3$], and Si(OSiMe$_3$)H$_2$[CH$_2$—Si(OiBu)$_3$].

In some embodiments, b=0 and c=2 to produce SiH$_2$[CH$_2$—Si(OR)$_x$H$_y$R$_z$]$_2$, wherein x=0 to 3; y=0-1; z=0-3; each R is independently a C1 to C5 linear or branched alkyl group or a trimethylsilyl group; and each R' is independently a C1 to C5 linear or branched alkyl group.

Exemplary compounds wherein b=0, c=2, x=3, y=0, and z=0 include SiH$_2$[CH$_2$—Si(OMe)$_3$]$_2$, SiH$_2$[CH$_2$—Si(OEt)$_3$]$_2$, SiH$_2$[CH$_2$—Si(OiPr)$_3$]$_2$, SiH$_2$[CH$_2$—Si(OnPr)$_3$]$_2$, SiH$_2$[CH$_2$—Si(OnBu)$_3$]$_2$, SiH$_2$[CH$_2$—Si(OtBu)$_3$]$_2$, and SiH$_2$[CH$_2$—Si(OiBu)$_3$]$_2$.

Exemplary compounds wherein b=0, c=2, x=0, y=0, and z=3 include SiH$_2$[CH$_2$—Si(Me)$_3$]$_2$, SiH$_2$[CH$_2$—Si(Et)$_3$]$_2$, SiH$_2$[CH$_2$—Si(iPr)$_3$]$_2$, SiH$_2$[CH$_2$—Si(nPr)$_3$]$_2$, SiH$_2$[CH$_2$—Si(nBu)$_3$]$_2$, SiH$_2$[CH$_2$—Si(tBu)$_3$]$_2$, SiH$_2$[CH$_2$—Si(iBu)$_3$]$_2$, and SiH$_2$[CH$_2$—Si(SiMe$_3$)$_3$]$_2$.

Exemplary compounds wherein b=0, c=2, x=2, y=1, and z=0 include SiH$_2$[CH$_2$—SiH(OMe)$_2$]$_2$, SiH$_2$[CH$_2$—SiH(OEt)$_2$]$_2$, SiH$_2$[CH$_2$—SiH(OiPr)$_2$]$_2$, SiH$_2$[CH$_2$—SiH(OnPr)$_2$]$_2$, SiH$_2$[CH$_2$—SiH(OnBu)$_2$]$_2$, SiH$_2$[CH$_2$—SiH(OtBu)$_2$]$_2$, SiH$_2$[CH$_2$—SiH(OiBu)$_2$]$_2$.

Exemplary compounds wherein b=0, c=2, x=0, y=1, and z=2 include SiH$_2$[CH$_2$—SiH(Me)$_2$]$_2$, SiH$_2$[CH$_2$—SiH(Et)$_2$]$_2$, SiH$_2$[CH$_2$—SiH(iPr)$_2$]$_2$, SiH$_2$[CH$_2$—SiH(nPr)$_2$]$_2$, SiH$_2$[CH$_2$—SiH(nBu)$_2$]$_2$, SiH$_2$[CH$_2$—SiH(tBu)$_2$]$_2$, SiH$_2$[CH$_2$—SiH(iBu)$_2$]$_2$, SiH$_2$[CH$_2$—SiH(SiMe$_3$)$_2$]$_2$.

Exemplary compounds wherein b=0, c=2, x=1, y=1, and z=1 include SiH$_2$[CH$_2$—SiH(Me)(OMe)]$_2$, SiH$_2$[CH$_2$—SiH(Me)(OEt)]$_2$, SiH$_2$[CH$_2$—SiH(Me)(OiPr)]$_2$, SiH$_2$[CH$_2$—SiH(Me)(OnPr)]$_2$, SiH$_2$[CH$_2$—SiH(Me)(OnBu)]$_2$, SiH$_2$[CH$_2$—SiH(Me)(OiBu)]$_2$, SiH$_2$[CH$_2$—SiH(Me)(OtBu)]$_2$, SiH$_2$[CH$_2$—SiH(Et)(OMe)]$_2$, SiH$_2$[CH$_2$—SiH(Et)(OEt)]$_2$, SiH$_2$[CH$_2$—SiH(Et)(OiPr)]$_2$, SiH$_2$[CH$_2$—SiH(Et)(OnPr)]$_2$, SiH$_2$[CH$_2$—SiH(Et)(OnBu)]$_2$, SiH$_2$[CH$_2$—SiH(Et)(OtBu)]$_2$, SiH$_2$[CH$_2$—SiH(Et)(OiBu)]$_2$, SiH$_2$[CH$_2$—SiH(iPr)(OMe)]$_2$, SiH$_2$[CH$_2$—SiH(iPr)(OEt)]$_2$, SiH$_2$[CH$_2$—SiH(iPr)(OiPr)]$_2$, SiH$_2$[CH$_2$—SiH(iPr)(OnPr)]$_2$, SiH$_2$[CH$_2$—SiH(iPr)(OnBu)]$_2$, SiH$_2$[CH$_2$—SiH(iPr)(OtBu)]$_2$, SiH$_2$[CH$_2$—SiH(iPr)(OiBu)]$_2$, SiH$_2$[CH$_2$—SiH(nPr)(OMe)]$_2$, SiH$_2$[CH$_2$—SiH(nPr)(OEt)]$_2$, SiH$_2$[CH$_2$—SiH(nPr)(OnPr)]$_2$, SiH$_2$[CH$_2$—SiH(nPr)(OiPr)]$_2$, SiH$_2$[CH$_2$—SiH(nPr)(OnBu)]$_2$, SiH$_2$[CH$_2$—SiH(nPr)(OtBu)]$_2$, SiH$_2$[CH$_2$—SiH(nPr)(OiBu)]$_2$, SiH$_2$[CH$_2$—SiH(nBu)(OMe)]$_2$, SiH$_2$[CH$_2$—SiH(nBu)(OEt)]$_2$, SiH$_2$[CH$_2$—SiH(nBu)(OnPr)]$_2$, SiH$_2$[CH$_2$—SiH(nBu)(OiPr)]$_2$, SiH$_2$[CH$_2$—SiH(nBu)(OnBu)]$_2$, SiH$_2$[CH$_2$—SiH(nBu)(OtBu)]$_2$, SiH$_2$[CH$_2$—SiH(nBu)(OiBu)]$_2$, SiH$_2$[CH$_2$—SiH(tBu)(OMe)]$_2$, SiH$_2$[CH$_2$—SiH(tBu)(OEt)]$_2$, SiH$_2$[CH$_2$—SiH(tBu)(OnPr)]$_2$, SiH$_2$[CH$_2$—SiH(tBu)(OiPr)]$_2$, SiH$_2$[CH$_2$—SiH(tBu)(OnBu)]$_2$, SiH$_2$[CH$_2$—SiH(tBu)(OtBu)]$_2$, SiH$_2$[CH$_2$—SiH(tBu)(OiBu)]$_2$, SiH$_2$[CH$_2$—SiH(iBu)(OMe)]$_2$, SiH$_2$[CH$_2$—SiH(iBu)(OEt)]$_2$, SiH$_2$[CH$_2$—SiH(iBu)(OnPr)]$_2$, SiH$_2$[CH$_2$—SiH(iBu)(OiPr)]$_2$, SiH$_2$[CH$_2$—SiH(iBu)(OnBu)]$_2$, SiH$_2$[CH$_2$—SiH(iBu)(OtBu)]$_2$, SiH$_2$[CH$_2$—SiH(iBu)(OiBu)]$_2$, SiH$_2$[CH$_2$—SiH(SiMe$_3$)(OMe)]$_2$, SiH$_2$[CH$_2$—SiH(SiMe$_3$)(OEt)]$_2$, SiH$_2$[CH$_2$—SiH(SiMe$_3$)(OnPr)]$_2$, SiH$_2$[CH$_2$—SiH(SiMe$_3$)(OiPr)]$_2$, SiH$_2$[CH$_2$—SiH(SiMe$_3$)(OnBu)]$_2$, SiH$_2$[CH$_2$—SiH(SiMe$_3$)(OtBu)]$_2$, and SiH$_2$[CH$_2$—SiH(SiMe$_3$)(OiBu)]$_2$.

Exemplary compounds wherein b=0, c=2, x=1, y=0, and z=2 include SiH$_2$[CH$_2$—Si(Me)$_2$(OMe)]$_2$, SiH$_2$[CH$_2$—Si(Me)$_2$(OEt)]$_2$, SiH$_2$[CH$_2$—Si(Me)$_2$(OiPr)]$_2$, SiH$_2$[CH$_2$—Si(Me)$_2$(OnPr)]$_2$, SiH$_2$[CH$_2$—Si(Me)$_2$(OnBu)]$_2$, SiH$_2$[CH$_2$—Si(Me)$_2$(OiBu)]$_2$, SiH$_2$[CH$_2$—Si(Me)$_2$(OtBu)]$_2$, SiH$_2$[CH$_2$—Si(Et)$_2$(OMe)]$_2$, SiH$_2$[CH$_2$—Si(Et)$_2$(OEt)]$_2$, SiH$_2$[CH$_2$—Si(Et)$_2$(OiPr)]$_2$, SiH$_2$[CH$_2$—Si(Et)$_2$(OnPr)]$_2$, SiH$_2$[CH$_2$—Si(Et)$_2$(OnBu)]$_2$, SiH$_2$[CH$_2$—Si(Et)$_2$(OtBu)]$_2$, SiH$_2$[CH$_2$—Si(Et)$_2$(OiBu)]$_2$, SiH$_2$[CH$_2$—Si(iPr)$_2$(OMe)]$_2$, SiH$_2$[CH$_2$—Si(iPr)$_2$(OEt)]$_2$, SiH$_2$[CH$_2$—Si(iPr)$_2$(OiPr)]$_2$, SiH$_2$[CH$_2$—Si(iPr)$_2$(OnPr)]$_2$, SiH$_2$[CH$_2$—Si(iPr)$_2$(OnBu)]$_2$, SiH$_2$[CH$_2$—Si(iPr)$_2$(OtBu)]$_2$, SiH$_2$[CH$_2$—Si(iPr)$_2$(OiBu)]$_2$, SiH$_2$[CH$_2$—Si(nPr)$_2$(OMe)]$_2$, SiH$_2$[CH$_2$—Si(nPr)$_2$(OEt)]$_2$, SiH$_2$[CH$_2$—Si(nPr)$_2$(OnPr)]$_2$, SiH$_2$[CH$_2$—Si(nPr)$_2$(OiPr)]$_2$, SiH$_2$[CH$_2$—Si(nPr)$_2$(OnBu)]$_2$, SiH$_2$[CH$_2$—Si(nPr)$_2$(OtBu)]$_2$, SiH$_2$[CH$_2$—Si(nPr)$_2$(OiBu)]$_2$, SiH$_2$[CH$_2$—Si(nBu)$_2$(OMe)]$_2$, SiH$_2$[CH$_2$—Si(nBu)$_2$(OEt)]$_2$, SiH$_2$[CH$_2$—Si(nBu)$_2$(OnPr)]$_2$, SiH$_2$[CH$_2$—Si(nBu)$_2$(OiPr)]$_2$, SiH$_2$[CH$_2$—Si(nBu)$_2$(OnBu)]$_2$, SiH$_2$[CH$_2$—Si(nBu)$_2$(OtBu)]$_2$, SiH$_2$[CH$_2$—Si(nBu)$_2$(OiBu)]$_2$, SiH$_2$[CH$_2$—Si(tBu)$_2$(OMe)]$_2$, SiH$_2$[CH$_2$—Si(tBu)$_2$(OEt)]$_2$, SiH$_2$[CH$_2$—Si(tBu)$_2$(OnPr)]$_2$, SiH$_2$[CH$_2$—Si(tBu)$_2$(OiPr)]$_2$, SiH$_2$[CH$_2$—Si(tBu)$_2$(OnBu)]$_2$, SiH$_2$[CH$_2$—Si(tBu)$_2$(OtBu)]$_2$, SiH$_2$[CH$_2$—Si(tBu)$_2$(OiBu)]$_2$, SiH$_2$[CH$_2$—Si(iBu)$_2$(OMe)]$_2$, SiH$_2$[CH$_2$—Si(iBu)$_2$(OEt)]$_2$, SiH$_2$[CH$_2$—Si(iBu)$_2$(OnPr)]$_2$, SiH$_2$[CH$_2$—Si(iBu)$_2$(OiPr)]$_2$, SiH$_2$[CH$_2$—Si(iBu)$_2$(OnBu)]$_2$, SiH$_2$[CH$_2$—Si(iBu)$_2$(OtBu)]$_2$, SiH$_2$[CH$_2$—Si(iBu)$_2$(OiBu)]$_2$, SiH$_2$[CH$_2$—Si(SiMe$_3$)$_2$(OMe)]$_2$, SiH$_2$[CH$_2$—Si(SiMe$_3$)$_2$(OEt)]$_2$, SiH$_2$[CH$_2$—Si(SiMe$_3$)$_2$(OnPr)]$_2$, SiH$_2$[CH$_2$—Si(SiMe$_3$)$_2$(OiPr)]$_2$, SiH$_2$[CH$_2$—Si(SiMe$_3$)$_2$(OnBu)]$_2$, SiH$_2$[CH$_2$—Si(SiMe$_3$)$_2$(OtBu)]$_2$, and SiH$_2$[CH$_2$—Si(SiMe$_3$)$_2$(OiBu)]$_2$.

Exemplary compounds wherein b=0, c=2, x=2, y=0, and z=1 include SiH$_2$[CH$_2$—Si(Me)(OMe)$_2$]$_2$, SiH$_2$[CH$_2$—Si(Me)(OEt)$_2$]$_2$, SiH$_2$[CH$_2$—Si(Me)(OiPr)$_2$]$_2$, SiH$_2$[CH$_2$—Si(Me)(OnPr)$_2$]$_2$, SiH$_2$[CH$_2$—Si(Me)(OnBu)$_2$]$_2$, SiH$_2$[CH$_2$—Si(Me)(OiBu)$_2$]$_2$, SiH$_2$[CH$_2$—Si(Me)(OtBu)$_2$]$_2$, SiH$_2$[CH$_2$—Si(Et)(OMe)$_2$]$_2$, SiH$_2$[CH$_2$—Si(Et)(OEt)$_2$]$_2$, SiH$_2$[CH$_2$—Si(Et)(OiPr)$_2$]$_2$, SiH$_2$[CH$_2$—Si(Et)(OnPr)$_2$]$_2$, SiH$_2$[CH$_2$—Si(Et)(OnBu)$_2$]$_2$, SiH$_2$[CH$_2$—Si(Et)(OtBu)$_2$]$_2$, SiH$_2$[CH$_2$—Si(Et)(OiBu)$_2$]$_2$, SiH$_2$[CH$_2$—Si(iPr)(OMe)$_2$]$_2$, SiH$_2$[CH$_2$—Si(iPr)(OEt)$_2$]$_2$, SiH$_2$[CH$_2$—Si(iPr)(OiPr)$_2$]$_2$, SiH$_2$[CH$_2$—Si(iPr)(OnPr)$_2$]$_2$, SiH$_2$[CH$_2$—Si(iPr)(OnBu)$_2$]$_2$, SiH$_2$[CH$_2$—Si(iPr)(OtBu)$_2$]$_2$, SiH$_2$[CH$_2$—Si(iPr)(OiBu)$_2$]$_2$, SiH$_2$[CH$_2$—Si(nPr)(OMe)$_2$]$_2$, SiH$_2$[CH$_2$—Si(nPr)(OEt)$_2$]$_2$, SiH$_2$[CH$_2$—Si(nPr)(OnPr)$_2$]$_2$, SiH$_2$[CH$_2$—Si(nPr)(OiPr)$_2$]$_2$, SiH$_2$[CH$_2$—Si(nPr)(OnBu)$_2$]$_2$, SiH$_2$[CH$_2$—Si(nPr)(OtBu)$_2$]$_2$, SiH$_2$[CH$_2$—Si(nPr)(OiBu)$_2$]$_2$, SiH$_2$[CH$_2$—Si(nBu)(OMe)$_2$]$_2$, SiH$_2$[CH$_2$—Si(nBu)(OEt)$_2$]$_2$, SiH$_2$[CH$_2$—Si(nBu)(OnPr)$_2$]$_2$, SiH$_2$[CH$_2$—Si(nBu)(OiPr)$_2$]$_2$, SiH$_2$[CH$_2$—Si(nBu)(OnBu)$_2$]$_2$, SiH$_2$[CH$_2$—Si(nBu)(OtBu)$_2$]$_2$, SiH$_2$[CH$_2$—Si(nBu)(OiBu)$_2$]$_2$, SiH$_2$[CH$_2$—Si(tBu)(OMe)$_2$]$_2$, SiH$_2$[CH$_2$—Si(tBu)(OEt)$_2$]$_2$, SiH$_2$[CH$_2$—Si(tBu)(OnPr)$_2$]$_2$, SiH$_2$[CH$_2$—Si(tBu)(OiPr)$_2$]$_2$, SiH$_2$[CH$_2$—Si(tBu)(OnBu)$_2$]$_2$, SiH$_2$[CH$_2$—Si(tBu)(OtBu)$_2$]$_2$, SiH$_2$[CH$_2$—Si(tBu)(OiBu)$_2$]$_2$, SiH$_2$[CH$_2$—Si(iBu)(OMe)$_2$]$_2$, SiH$_2$[CH$_2$—Si(iBu)(OEt)$_2$]$_2$, SiH$_2$[CH$_2$—Si(iBu)(OnPr)$_2$]$_2$, SiH$_2$[CH$_2$—Si(iBu)(OiPr)$_2$]$_2$, SiH$_2$[CH$_2$—Si(iBu)(OnBu)$_2$]$_2$, SiH$_2$[CH$_2$—Si(iBu)(OtBu)$_2$]$_2$, SiH$_2$[CH$_2$—Si(iBu)(OiBu)$_2$]$_2$, SiH$_2$[CH$_2$—Si(SiMe$_3$)(OMe)$_2$]$_2$, SiH$_2$[CH$_2$—Si(SiMe$_3$)(OEt)$_2$]$_2$, SiH$_2$[CH$_2$—Si(SiMe$_3$)(OnPr)$_2$]$_2$, SiH$_2$[CH$_2$—Si(SiMe$_3$)(OiPr)$_2$]$_2$, SiH$_2$[CH$_2$—Si(SiMe$_3$)(OnBu)$_2$]$_2$, SiH$_2$[CH$_2$—Si(SiMe$_3$)(OtBu)$_2$]$_2$, and SiH$_2$[CH$_2$—Si(SiMe$_3$)(OiBu)$_2$]$_2$.

The disclosed compounds are synthesized by reacting a Grignard reagent having the formula Si(OR')$_x$H$_y$R$_z$(CH$_2$MgX) with a quenching agent having the formula SiCl$_a$ $(OR)_b(H)_c$, wherein a=1 to 3; b=0 to 3; c=0 to 2; a+b+c=4; x=0 to 3; y=0 to 1; z=0 to 3; x+y+z=3; X=Cl, Br, or I ("halide" atoms); each R is independently a C1 to C5 linear or branched alkyl group or a trimethylsilyl group; and each R' is independently a C1 to C5 linear or branched alkyl group.

The Grignard reagent and the quenching agent are reacted in a polar solvent, such as tetrahydrofuran, diethyl ether, or dimethoxyethane. The molar ratio of Grignard reagent to quenching agent is between approximately 0.8 to approximately 4.5. The number of halide atoms in the quenching agent further determines the molar ratio of Grignard reagent to quenching agent. For example, if the quenching agent contains one halide atom, the molar ratio of Grignard reagent to quenching agent should range from 0.8 to 1.5. If the quenching agent contains two halide atoms, the molar ratio of Grignard reagent to quenching agent should range from 1.6 to 3. If the quenching agent contains three halide atoms, the molar ratio of Grignard reagent to quenching agent should range from 2.4 to 4.5.

The quenching agent "deactivates" the Grignard reagent by reacting with the Grignard reagent to produce the disclosed compound and a Mg salt compound. This quenching action prevents the Grignard reagent from reacting with itself and producing undesired products, such as trisilacyclohexane compounds. The number of halide molecules in the quenching agent further determines the number of silicon molecules in the disclosed compound (not including the Si atom in any pendant trimethylsilyl groups). For example, if the quenching agent contains one halide atom, the disclosed compound will contain two silicon atoms. If the quenching agent contains two halide atoms, the disclosed compound will contain three silicon atoms. If the quenching agent contains three halide atoms, the disclosed compound will contain four silicon atoms.

In situ quenching occurs when the Grignard reagent, as it forms, immediately reacts with the quenching agent. As will be described in more detail infra, the quenching agent and the $Si(OR')_xH_yR_z(CH_2X)$ reactant used to form the Grignard reagent may be mixed prior to reaction with magnesium, wherein x=0 to 3; y=0 to 1; z=0 to 3; x+y+z=3; each R is independently a C1 to C5 linear or branched alkyl group or a trimethylsilyl group; and each R' is independently a C1 to C5 linear or branched alkyl group.

Preferably, the Grignard reagent and quenching agent are mixed in an anhydrous polar solvent, resulting in improved yield. One of ordinary skill in the art will recognize how to produce the anhydrous polar solvent. For example, the polar solvent, benzophenone, and sodium may be mixed and refluxed, followed by distillation (referred to as Na treated). Alternatively, the polar solvent may be filtered through activated alumina and then degassed by $N_2$ bubbling.

The Grignard reagent and the quenching agent may be mixed with the polar solvent at temperatures ranging from approximately 0° C. to approximately 70° C., preferably from approximately 0° C. to approximately 50° C. One of ordinary skill in the art will recognize that the reaction is exothermic and therefore that the temperature of the reaction may increase as the reaction progresses. The mixing may occur for a duration of approximately 1 hour to approximately 48 hours, preferably for approximately 8 hours. One of ordinary skill in the art will recognize that the duration of the reaction will depend upon the temperature and the number of chlorine atoms in the quenching agent, with more chlorine atoms requiring a longer reaction time. One of ordinary skill in the art will further recognize that these reactions must be performed in an inert, anhydrous atmosphere, preferably under a nitrogen atmosphere.

After mixing, the polar solvent may be removed by distillation. The remaining material is mixed with a nonpolar solvent, such as pentane, hexane, or heptane, and subsequently filtered to produce the desired compound.

Applicants believe that the alkoxy group of the quenching agents causes the Grignard reagents to preferentially react with the at least one Si—Cl bond of the quenching agents. In other words, the alkoxy group acts as a protecting group to the Si atom during the reaction of the Grignard reagent with the quenching agent. Similarly, Applicants have surprisingly discovered that the hydride ligand of the quenching agents remains inert during the reaction of Grignard reagent and the quenching agent, once again causing the Grignard reagent to preferentially react with the at least one Si—Cl bond of the quenching agent. The use of the hydrogen or alkoxy group provides the ability of the disclosed synthesis methods to selectively generate the target compound in high yield. In contrast, as illustrated in the following comparative example, use of $SiCl_4$ as the quenching agent yields the undesirable mixture of $SiCl_{4-x}(CH_2—Si(OEt)_3)_x$ (x=1, 2, 3).

In some embodiments, a=2, b=2, and c=0 to produce quenching agents having the formula $SiCl_2(OR)_2$, wherein each R is independently a C1 to C5 linear or branched alkyl group or a trimethylsilyl group. Exemplary quenching agents include $SiCl_2(OMe)_2$, $SiCl_2(OEt)_2$, $SiCl_2(OiPr)_2$, $SiCl_2(OnPr)_2$, $SiCl_2(OnBu)_2$, $SiCl_2(OtBu)_2$, $SiCl_2(OsBu)_2$, $SiCl_2(OPentane)_2$, or $SiCl_2(OSiMe_3)_2$. These quenching agents are not commercially available, but may be synthesized by methods known in the art.

In some embodiments, b=0 to produce quenching agents having the formula $SiCl_a(H)_{4-a}$, wherein a=1 to 1 Exemplary quenching agents include $SiClH_3$, $SiH_2Cl_2$, or $SiHCl_3$. These quenching agents are commercially available.

In some embodiments, c=2 to produce quenching agents having the formula $SiCl_a(OR)_{2-a}H_2$, wherein a=1-2 and each R is independently a C1 to C5 linear or branched alkyl group or a trimethylsilyl group. Exemplary quenching agents include $SiH_2Cl_2$, $SiH_2Cl(OMe)$, $SiH_2Cl(OEt)$, $SiH_2Cl(OiPr)$, $SiH_2Cl(OnPr)$, $SiH_2Cl(OnBu)$, $SiH_2Cl(OtBu)$, $SiH_2Cl(OsBu)$, $SiH_2Cl(O-Pentane)$, or $SiH_2Cl(OSiMe_3)$. These quenching agents are commercially available.

In some embodiments, b=0 and c=2 to produce the quenching agent $SiCl_2H_2$. This quenching agent is commercially available.

In some embodiments, x=3, y=0, z=0, and R'=Me or Et to produce Grignard reagents having the formula $Si(OMe)_3(CH_2MgX)$ or $Si(OEt)_3(CH_2MgX)$, wherein X=Cl, Br, or I. Exemplary reagents include $Si(OMe)_3(CH_2MgCl)$, $Si(OEt)_3(CH_2MgCl)$, $Si(OMe)_3(CH_2MgBr)$, $Si(OEt)_3(CH_2MgBr)$, $Si(OMe)_3(CH_2MgI)$, and $Si(OEt)_3(CH_2MgI)$.

In some embodiments, y=1 to produce Grignard reagents having the formula $SiH(OR')_x(R)_{2-x}(CH_2MgX)$, wherein x=0 to 2; X=Cl, Br, or I; each R is independently a C1 to C5 linear or branched alkyl group or a trimethylsilyl group; and each R' is independently a C1 to C5 linear or branched alkyl group. Exemplary reagents include $SiH(OMe)_2(CH_2MgCl)$, $SiH(OMe)_2(CH_2MgBr)$, $SiH(OMe)_2(CH_2MgI)$, $SiH(OEt)_2(CH_2MgCl)$, $SiH(OEt)_2(CH_2MgBr)$, $SiH(OEt)_2(CH_2MgI)$, $SiH(OiPr)_2(CH_2MgCl)$, $SiH(OiPr)_2(CH_2MgBr)$, $SiH(OiPr)_2(CH_2MgI)$, $SiH(OnPr)_2(CH_2MgCl)$, $SiH(OnPr)_2(CH_2MgBr)$, $SiH(OnPr)_2(CH_2MgI)$, $SiH(OnBu)_2(CH_2MgCl)$, $SiH(OnBu)_2(CH_2MgBr)$, $SiH(OnBu)_2(CH_2MgI)$, $SiH(OtBu)_2(CH_2MgCl)$, $SiH(OtBu)_2(CH_2MgBr)$, $SiH(OtBu)_2(CH_2MgI)$, $SiH(OMe)(Me)(CH_2MgCl)$, $SiH(OMe)(Me)(CH_2MgBr)$, $SiH(OMe)(Me)(CH_2MgI)$, $SiH(OEt)(Et)(CH_2MgCl)$, $SiH(OEt)(Et)(CH_2MgBr)$, $SiH(OEt)(Et)(CH_2MgI)$, $SiH(OiPr)(iPr)$ (CH$_2$MgCl), SiH(OiPr)(iPr)(CH$_2$MgBr), SiH(OiPr)(iPr) (CH$_2$MgI), SiH(OnPr)(nPr)(CH$_2$MgCl), SiH(OnPr)(nPr) (CH$_2$MgBr), SiH(OnPr)(nPr)(CH$_2$MgI), SiH(OnBu)(nBu) (CH$_2$MgCl), SiH(OnBu)(nBu)(CH$_2$MgBr), SiH(OnBu) (nBu)(CH$_2$MgI), SiH(OtBu)(tBu)(CH$_2$MgCl), SiH(OtBu) (tBu)(CH$_2$MgBr), SiH(OtBu)(tBu)(CH$_2$MgI), SiH(OMe) (SiMe$_3$)(CH$_2$MgCl), SiH(OMe)(SiMe$_3$)(CH$_2$MgBr), SiH (OMe)(SiMe$_3$)(CH$_2$MgI), SiHMe$_2$(CH$_2$MgCl), SiHMe$_2$ (CH$_2$MgBr), SiHMe$_2$(CH$_2$MgI), SiHEt$_2$(CH$_2$MgCl), SiHEt$_2$ (CH$_2$MgBr), SiHEt$_2$(CH$_2$MgI), SiH(iPr)$_2$(CH$_2$MgCl), SiH (iPr)$_2$(CH$_2$MgBr), SiH(iPr)$_2$(CH$_2$MgI), SiH(nPr)$_2$ (CH$_2$MgCl), SiH(nPr)$_2$(CH$_2$MgBr), SiH(nPr)$_2$(CH$_2$MgI), SiH(nBu)$_2$(CH$_2$MgCl), SiH(nBu)$_2$(CH$_2$MgBr), SiH(nBu)$_2$ (CH$_2$MgI), SiH(tBu)$_2$(CH$_2$MgCl), SiH(tBu)$_2$(CH$_2$MgBr), SiH(tBu)$_2$(CH$_2$MgI), SiH(SiMe$_3$)$_2$(CH$_2$MgCl), SiH (SiMe$_3$)$_2$ (CH$_2$MgBr), or SiH(SiMe$_3$)$_2$(CH$_2$MgI).

In some embodiments, z=0 to produce Grignard reagents having the formula Si(OR')$_x$H$_y$(CH$_2$MgX), wherein x=0 to 3; y=0 to 1; x+y=3; X=Cl, Br, or I; and each R' is independently a C1 to C5 linear or branched alkyl group. Exemplary reagents include Si(OMe)$_3$(CH$_2$MgCl), Si(OEt)$_3$ (CH$_2$MgCl), Si(OMe)$_3$(CH$_2$MgBr), Si(OEt)$_3$(CH$_2$MgBr), Si(OMe)$_3$(CH$_2$MgI), Si(OEt)$_3$(CH$_2$MgI), Si(OiPr)$_3$ (CH$_2$MgCl), Si(OiPr)$_3$(CH$_2$MgBr), Si(OiPr)$_3$(CH$_2$MgI), Si(OnPr)$_3$(CH$_2$MgCl), Si(OnPr)$_3$(CH$_2$MgBr), Si(OnPr)$_3$ (CH$_2$MgI), SiH(OMe)$_2$(CH$_2$MgCl), SiH(OMe)$_2$ (CH$_2$MgBr), SiH(OMe)$_2$(CH$_2$MgI), SiH(OEt)$_2$(CH$_2$MgCl), SiH(OEt)$_2$(CH$_2$MgBr), SiH(OEt)$_2$(CH$_2$MgI), SiH(OiPr)$_2$ (CH$_2$MgCl), SiH(OiPr)$_2$(CH$_2$MgBr), SiH(OiPr)$_2$(CH$_2$MgI), SiH(OnPr)$_2$(CH$_2$MgCl), SiH(OnPr)$_2$(CH$_2$MgBr), SiH (OnPr)$_2$(CH$_2$MgI), SiH(OnBu)$_2$(CH$_2$MgCl), SiH(OnBu)$_2$ (CH$_2$MgBr), SiH(OnBu)$_2$(CH$_2$MgI), SiH(OtBu)$_2$ (CH$_2$MgCl), SiH(OtBu)$_2$(CH$_2$MgBr), or SiH(OtBu)$_2$ (CH$_2$MgI).

The Grignard reagents may be synthesized by reacting Si(OR')$_x$H$_y$R$_z$(CH$_2$X) over magnesium, wherein x=0 to 3; y=0 to 1; z=0 to 3; x+y+z=3; each R is independently a C1 to C5 linear or branched alkyl group or a trimethylsilyl group; and each R' is independently a C1 to C5 linear or branched alkyl group. The Si(OR')$_x$H$_y$R$_z$(CH$_2$X) reactants are commercially available.

The synthesis of the Grignard reagent may occur in the same vessel as that in which the Grignard reagent and the quenching agent are reacted. The Si(OR')$_x$H$_y$R$_z$(CH$_2$X) reactant and quenching agent may be mixed together before reaction with magnesium. Alternatively, the Si(OR')$_x$H$_y$R$_z$ (CH$_2$X) reactant may be added to the Grignard reagent, followed by addition of the quenching agent. One of ordinary skill in the art will recognize that addition of an activator, such as 1,2-dibromoethane (BrCH$_2$CH$_2$Br), iodide (I$_2$), or pure HCl, may be needed to activate the Mg surface. The activator may be added to the Grignard reagent before addition of the Si(OR')$_x$H$_y$R$_z$(CH$_2$X) reactant and/or quenching agent.

The OR' alkoxy group of the Si(OR')$_x$H$_y$R$_z$(CH$_2$X) reactant is more reactive than the R alkyl group. As a result, upon exposure to Mg, the Si(OR')$_x$H$_y$R$_z$(CH$_2$X) reactant may react upon itself to form the cyclic molecule (—CH$_2$—Si(OR')$_x$ H$_y$R$_z$—)$_3$. Therefore, when the reactant contains at least one alkoxy group, the synthesis of the Grignard reagent preferably occurs in the same vessel as that in which the reaction between the Grignard reagent and the quenching agent occurs. In this embodiment, the Si(OR')$_x$H$_y$R$_z$(CH$_2$X) reactant, Mg, and the quenching agent are added to a flask containing the polar solvent and mixed (i.e., in situ quenching). The Mg may be activated by an activator prior to adding the Si(OR')$_x$H$_y$R$_z$(CH$_2$X) reactant and the quenching agent. The quenching agent prevents the Grignard reagent formed by the reaction of the Si(OR')$_x$H$_y$R$_z$(CH$_2$X) reactant and the Mg from reacting with itself and producing undesired products, such as trisilacyclohexane compounds. The quenching agent "deactivates" the Grignard reagent by reacting with the Grignard reagent to produce the disclosed compound and a Mg salt compound. The mixing may occur at temperatures ranging from approximately 0° C. to approximately 70° C., preferably from approximately 0° C. to approximately 50° C. One of ordinary skill in the art will recognize that the reaction is exothermic and therefore that the temperature of the reaction may increase as the reaction progresses. The mixing is completed when no Mg remains.

After mixing, the polar solvent may be removed by distillation. The remaining material is mixed with a nonpolar solvent, such as pentane, butane, or hexane, and subsequently filtered to produce the desired compound.

The synthesized compounds may be reduced to form a compound having the formula SiH$_{b+c}$[CH$_2$—SiH$_{x+y}$R$_z$]$_{4-b-c}$, wherein b=0 to 3; c=0 to 2; b+c=1 to 3; x=0 to 3; y=0 to 1; z=0 to 3; x+y+z=3; and each R is independently a C1 to C5 linear or branched alkyl group or a trimethylsilyl group. AlLiH$_4$ in ether may be used as the reducing agent. The molar ratio of AlLiH$_4$ to Si(OR)$_b$(H)$_c$[CH$_2$—Si(OR')$_x$H$_y$R$_z$]$_a$ is between approximately (b+ax)/4 and approximately (b+ax)/2, wherein b=0 to 3, a=1 to 3, and x=0 to 3. Preferably, the molar ratio of AlLiH4 to Si(OR)$_b$(H)$_c$[CH$_2$—Si(OR')$_x$H$_y$R$_z$]$_a$ is approximately 1.2[(b+ax)/4] to approximately 1.5[(b+ax)/4]. NaBH$_4$ in ether may alternately be used as the reducing agent. The molar ratio of NaBH$_4$ to Si(OR)$_b$(H)$_c$[CH$_2$—Si(OR)$_x$ H$_y$R]$_a$ is between (b+ax)/4 and approximately (b+ax)/2, wherein b=0 to 3, a=1 to 3, and x=0 to 3. Preferably, the molar ratio of AlLiH4 to Si(OR)$_b$(H)$_c$[CH$_2$—Si(OR')$_x$H$_y$R$_z$]$_a$ is approximately 1.2[(b+ax)/4] to approximately 1.5[(b+ax)/4]. During reduction, the at least one alkoxy group of the quenching agent that had formerly acted as a protecting group is reactive to the reducing agent and easily reduced to H.

In one preferred embodiment, Si(OEt)$_2$[CH$_2$—Si(OEt)$_3$]$_2$ is synthesized by reacting a Grignard reagent having the formula Si(OEt)$_3$(CH$_2$MgCl) with a compound having the formula Si(OEt)$_2$Cl$_2$. The Si(OEt)$_3$(CH$_2$MgCl) Grignard reagent is formed in situ by reacting Si(OEt)$_3$(CH$_2$Cl) over magnesium. Addition of an activator may be necessary to activate the Mg surface. The Si(OEt)$_3$(CH$_2$MgCl) Grignard reagent may be formed in the same vessel as that in which the Grignard reagent and the quenching agent are reacted. Preferably, the Si(OEt)$_3$(CH$_2$MgCl) Grignard reagent is formed in the same vessel as that in which the Grignard reagent and the quenching agent are reacted.

Si(OEt)$_2$[CH$_2$—Si(OEt)$_3$]$_2$ may be reduced to form a compound having the formula SiH$_2$[CH$_2$—SiH$_3$]$_2$. AlLiH$_4$ in ether may be used as the reducing agent. The molar ratio of AlLiH$_4$ to Si(OEt)$_2$[CH$_2$—Si(OEt)$_3$]$_2$ is approximately 2. Alternatively, NaBH$_4$ in ether may be the reducing agent. The molar ratio of NaBH$_4$ to Si(OEt)$_2$[CH$_2$—Si(OEt)$_3$]$_2$ is approximately 2.

EXAMPLES

The following examples illustrate experiments performed in conjunction with the disclosure herein. The examples are not intended to be all inclusive and are not intended to limit the scope of disclosure described herein.

Comparative Example 2 molar equivalents ClCH$_2$Si(OEt)$_3$, 2 molar equivalents of Mg (sanded ribbon) and 1 molar equivalent of SiCl$_4$ were mixed with tetrahydrofuran (THF) (Na treated) in flask. The mixture was stirred until Mg disappeared and THF was removed by distillation. Pentane was added to extract a mixture including the $(EtO)_3SiCH_2Si(Cl)_2CH_2Si(OEt)_3$ product. After removal of pentane, 71% crude yield was obtained, including impurities formed by the reaction of 3 $ClMgCH_2$—$Si(OEt)_3$ molecules with $SiCl_4$, yielding $SiCl(CH_2$—$Si(OEt)_3)_3$.

Upon reduction by $AlLiH_4$ in ether, the obtained reduced mixture (all Cl or OEt being substituted by H to form the target compound $H_3SiCH_2SiH_2CH_2SiH_3$) is analyzed by gas chromatography shown in FIG. 1, showing a large concentration of branched carbosilane $SiH(CH_2$—$SiH_3)_3$ and partially reacted product $(CH_2(SiH_3)_2)$.

Example 1

Figure 2:
FIG. 2 is a GC/MS graph of the product synthesized in the Example.

2 molar equivalents of $ClCH_2Si(OEt)_3$, 2 molar equivalents of Mg (sanded ribbon), and molar 1 equivalent of $SiCl_2(OEt)_2$ were added in flask with THF (Na treated) under $N_2$. The mixture was stirred at room temperature until Mg disappeared. THF was removed by distillation. Pentane was added to extract the intermediate and then filtered to separate solid. After distillation of pentane, >90% yield crude $(EtO)_3Si$—$CH_2$—$Si(OEt)_2$-$CH_2$—$Si(OEt)_3$ was obtained. $(EtO)_3Si$—$CH_2$—$Si(OEt)_2$-$CH_2$—$Si(OEt)_3$ was directly reduced without further purification by 3 molar equivalents (based on the amount of $(EtO)_3Si$—$CH_2$—$Si(OEt)_2$-$CH_2$—$Si(OEt)_3$) of $LiAlH_4$ in ether in ice bath under $N_2$. The mixture was stirred for ~6 hours at room temperature. The volatiles were separated from solid by-products and $LiAlH_4$ by vacuum transfer, and ether was removed from the collected volatiles by distillation using a 55° C. bath. The final distillation give pure trisilapentane (TSP) as 70% overall yield. The pure TSP was analysed by GC as shown in FIG. 2, which indicates no undesired by-products remain. TSP: 1H NMR (C6D6): δ 3.95 (p, 2H, SiH2), 3.67 (t, 6H, SiH3), −0.40 (m, 4H, CH2). MS, m/z: 120 [M+].

Example 2

A 3-neck 100 mL flask equipped with a dry ice condenser, gas inlet tubing adapter, and a gas inlet adapter was charged with 50 mL of THF. The flask was cooled by dry ice to −40° C., the dry ice condenser was also filled with dry ice. 4.6 g (0.045 mol) of DCS ($SiH_2Cl_2$) was condensed into the flask using mass flow controller with a flow rate of 180-190 mL/min. 19.4 g (0.091 mol) of $(OEt)_3SiCH_2Cl$ was added to the DCS solution by syringe. A 250 mL 3-neck flask equipped with a dry ice condenser, thermometer, and torion 14 adapter was charged with Mg turnings (2.21 g, 0.091 mol) and 50 mL of THF. The mixture was cooled by ice bath to 5° C., and the condenser was filled with dry ice. The solution of DCS and $(OEt)_3SiCH_2Cl$ was slowly added to Mg suspension via 22 gauge canula. After ~10 mL of the solution was added, 0.1 mL of $BrCH_2CH_2Br$ was added to the reaction mixture to initiate the reaction. The rest of DCS solution was added within 30 min. The mixture was stirred at 5° C. for ~2 h. The ice bath was removed and the mixture was warmed up to room temperature while maintaining the dry ice condenser filled with dry ice. The mixture was stirred for 3 days at room temperature before all Mg disappeared. The mixture was filtered through Celite brand diatomaceous earth. The solids were washed with 2×20 mL of pentane. The solvents were removed from the filtrate under vacuum. The residue was mixed with 50 mL of pentane, and the mixture was filtered through Celite brand diatomaceous earth to remove the rest of the solids. Pentane was removed from the clear yellowish filtrate under vacuum leaving 10.4 g of $(EtO)_3Si$—$CH_2$—$SiH_2$—$CH_2$—$Si(OEt)_3$ (the target compound) and un-reacted $(OEt)_3SiCH_2Cl$ (60% yield of the target compound).

The target compound was reduced using $AlLiH_4$ (2.4 equivalents) in diethylether similarly to the other example, yielding 1,3,5-trisilapetane.

While embodiments of this invention have been shown and described, modifications thereof can be made by one skilled in the art without departing from the spirit or teaching of this invention. The embodiments described herein are exemplary only and not limiting. Many variations and modifications of the composition and method are possible and within the scope of the invention. Accordingly the scope of protection is not limited to the embodiments described herein, but is only limited by the claims which follow, the scope of which shall include all equivalents of the subject matter of the claims.

We claim:

1. A method of synthesizing a carbosilane compound comprising reacting a Grignard reagent having the formula $Si(OEt)_3(CH_2MgCl)$ with a quenching agent having the formula $Si(OEt)_2Cl_2$ to produce $Si(OEt)_2[CH_2$—$Si(OEt)_3]_2$.

2. The method of claim 1, further comprising forming the Grignard reagent $Si(OEt)_3(CH_2MgCl)$ by reacting $Si(OEt)_3(CH_2X)$ over magnesium.

3. The method of claim 2, wherein the step of forming the Grignard reagent $Si(OEt)_3(CH_2MgCl)$ occurs in a same vessel as the step of reacting the Grignard reagent and the quenching agent.

4. The method of claim 1, further comprising reducing $Si(OEt)_2[CH_2$—$Si(OEt)_3]_2$ to form a compound having a formula $SiH_2[CH_2$—$SiH_3]_2$.

\* \* \* \* \*